(12) United States Patent
Lanter et al.

(10) Patent No.: US 6,544,976 B1
(45) Date of Patent: Apr. 8, 2003

(54) NEUROTROPHIC 2-AZETIDINECARBOXYLIC ACID DERIVATIVES, AND RELATED COMPOSITIONS AND METHODS

(75) Inventors: James C. Lanter, Hillsborough, NJ (US); Suying Zhang, New Providence, NJ (US); Boyu Zhao, Lansdale, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/592,531

(22) Filed: Jun. 12, 2000

Related U.S. Application Data

(60) Provisional application No. 60/143,001, filed on Jul. 9, 1999.

(51) Int. Cl.[7] .................. A01N 43/00; C07D 205/00; C07D 205/08
(52) U.S. Cl. ............... 514/210; 540/200; 540/354
(58) Field of Search .................. 514/423, 422, 514/210; 548/533, 536, 517, 526, 527; 540/200, 354

(56) References Cited

U.S. PATENT DOCUMENTS

| | | | |
|---|---|---|---|
| 5,294,603 A | 3/1994 | Rinehart | 514/10 |
| 5,614,547 A | 3/1997 | Hamilton et al. | 514/423 |
| 5,696,135 A | 12/1997 | Steiner et al. | 514/317 |
| 5,721,256 A | 2/1998 | Hamilton et al. | 514/330 |
| 5,795,908 A | 8/1998 | Hamilton et al. | 514/423 |
| 5,798,355 A | 8/1998 | Steiner et al. | 514/248 |
| 5,801,187 A | 9/1998 | Li et al. | 514/365 |
| 5,801,197 A | 9/1998 | Steiner et al. | 514/548 |

FOREIGN PATENT DOCUMENTS

| | | |
|---|---|---|
| WO | WO 92/19593 | 11/1992 |
| WO | WO94/07858 | 4/1994 |
| WO | WO 94/08992 A1 | 4/1994 |
| WO | WO96/40140 | 12/1996 |
| WO | WO96/40633 | 12/1996 |
| WO | WO 96/40682 A1 | 12/1996 |
| WO | WO97/16190 | 5/1997 |
| WO | WO98/13343 | 4/1998 |
| WO | WO98/13355 | 4/1998 |
| WO | WO98/25950 | 6/1998 |
| WO | WO98/29116 | 7/1998 |
| WO | WO98/29117 | 7/1998 |
| WO | WO98/37882 | 9/1998 |
| WO | WO98/37885 | 9/1998 |
| WO | WO 99/32480 A1 | 7/1999 |
| WO | WO99/45006 | 9/1999 |

OTHER PUBLICATIONS

Brinton R.D. and Yamazaki, R.S., *Pharm. Res.*, 1998, 15, 386–398.

(List continued on next page.)

*Primary Examiner*—Alan L. Rotman
*Assistant Examiner*—Raymond Covington

(57) ABSTRACT

This invention provides compounds having the following general structure:

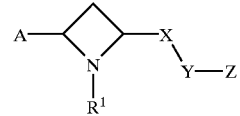

This invention also provides pharmaceutical compositions comprising same and methods of using these compositions to treat and prevent disorders characterized by neuronal damage.

20 Claims, 1 Drawing Sheet

OTHER PUBLICATIONS

Pahwa, R. and Kollr, W.C., *Drugs Today,* 1998, 34, 95–105.

Louvel, E., Hugon, J. and Doble, A., *Trends Pharmacol. Sci.,* 1997, 18, 196–203.

Biessels, G. J. and Van Dam, P.S., *Neurosci. Res. Commun.,* 1997, 20, 1–10.

Tomlinson, D.R., Fernyhough, P. and Diemel, L.T., *Diabetes,* 1997, 46 (suppl. 2) S43–S–49.

Hamilton, G.S., *Chem. Ind.,* (London) 1998, 4, 127–132.

Ebadi, M., et al., *Neurochem. Int.,* 1997, 30, 347–374.

Lyons, W. E., et al. (*Proc. Natl. Acad. Sci.*, 1994, 91 (8), 3191–5).

Hoshino, J. Hiraoka, J., Hata Y., Sawada, S., Yamamoto, Y. *J. Chem. Soc., Perkin Trans. 1* 1995, 6, 693–697.

Moehrle, H., Specks, F. *Arch. Pharm.* (Weinheim, Ger.) 1975, 308, 23–33.

Hawes, E.M., Davis, H.L. *J. Het. Chem.* 1973, 10, 39–42.

PCT Search Report for PCT/US 00/16136 dated Sep. 25, 2000.

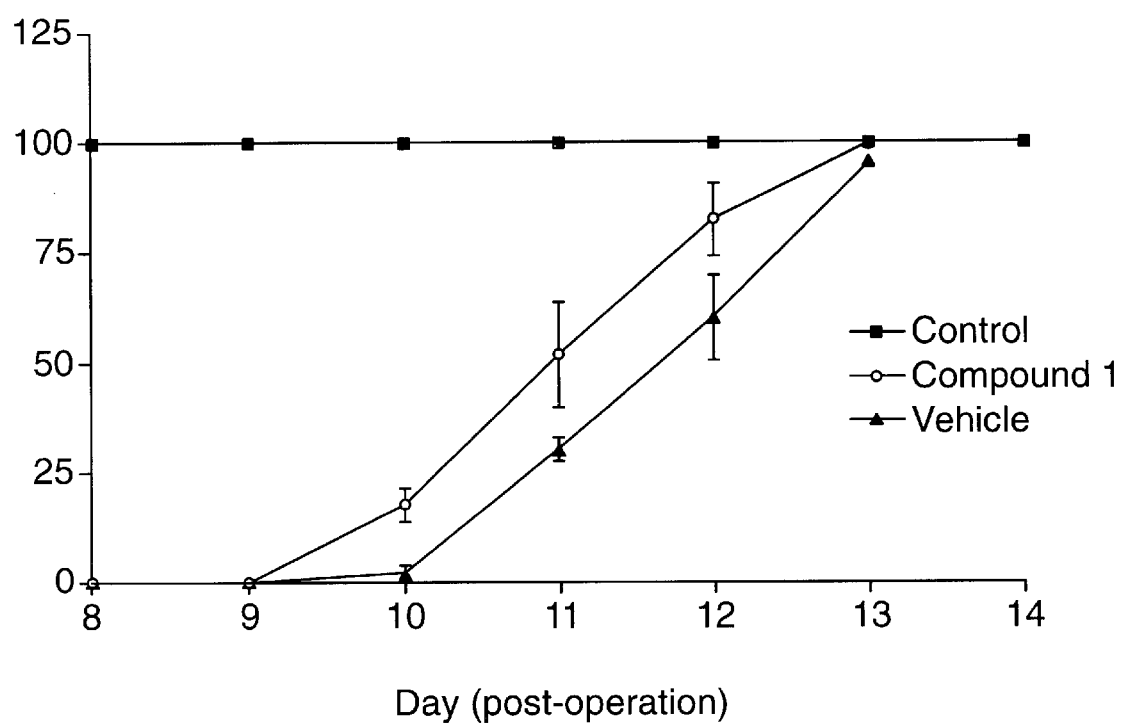

NEUROTROPHIC 2-AZETIDINECARBOXYLIC ACID DERIVATIVES, AND RELATED COMPOSITIONS AND METHODS

This application is related to U.S. Provisional Application Ser. No. 60/143,001 filed on Jul. 9, 1999.

FIELD OF THE INVENTION

This invention relates to novel 2-azetidinecarboxylic acid derivatives having neurotrophic activity. These compounds, along with related compositions and methods, are useful in the treatment and prevention of neuronal disorders such as Parkinson's disease, Alzheimer's disease, stroke, multiple sclerosis, amyotrophic lateral sclerosis, diabetic neuropathy and Bell's palsy.

BACKGROUND OF THE INVENTION

Neurodepenerative Diseases

Neurodegenerative diseases constitute a major threat to public health throughout the world. One of the most serious such diseases is Alzheimer's disease ("AD"), a major cause of dementia in aged humans and the fourth most common medical cause of death in the United States. In the U.S., it is estimated that AD afflicts two to three million individuals overall, and more than 5% of the population over the age of 65. Although the exact etiology of AD remains to be defined, the disease is characterized by the presence of a large number of amyloid plaques and neurofibrillary tangles in regions of the brain involved in cognitive function, and degeneration of cholinergic neurons that ascend from the basal forebrain to cortical and hippocampal areas. Currently, there are no effective therapies for AD. Brinton, R. D. and Yamazaki, R. S., *Pharm. Res.,* 1998, 15, 386–398.

Similar to AD, Parkinson's Disease ("PD") is a progressive degenerative disease of the central nervous system ("CNS"). The lifetime incidence of the disease is approximately 2% in the general population. In PD, degeneration of the dopaminergic neurons of the substantia nigra leads to a decrease in dopamine levels in the region of the brain controlling voluntary movement, the corpus striatum. Therefore, standard treatments have focused on the administration of agents, like L-dopa and bromocriptine, which replenish dopamine levels in the affected areas of the brain. Dopaminergic regimens lose their efficacy, however, as nerve cells continue to die and the disease progresses. At the same time, the involuntary tremors seen in the early stages of PD advance to periods of difficult movement and, ultimately, to immobility. Therefore, alternative therapies are actively being sought. Pahwa, R. and Koller, W. C., *Drugs Today,* 1998, 34, 95–105.

Neurodegenerative diseases of the somatosensory nervous system also constitute a class of debilitating and potentially lethal conditions. Amyotrophic lateral sclerosis ("ALS") is a fatal disease characterized by progressive degeneration of the upper and lower motor neurons. Although the precise etiology of ALS is unknown, popular theories suggest that excitotoxicity and/or oxidative stress are contributing factors. Riluzole is the first drug approved and marketed for ALS. It possesses antiexcitotoxic properties and has been shown to increase the rate of survival of ALS patients. However, the drug is not a cure, and clinical trials of alternative agents are currently underway. Louvel, E., Hugon, J. and Doble, A., *Trends Pharmacol. Sci.,* 1997, 18, 196–203.

Peripheral neuropathies are secondary to a number of metabolic and vascular conditions. In particular, approximately 30% of patients with diabetes mellitus suffer from some form of peripheral neuropathy that may affect the small myelinated fibers, causing loss of pain and temperature sensation, or the large fibers, causing motor or somatosensory defects. Pharmacotherapeutic intervention tends to be symptomatic, and the best approach to treatment and prevention remains the maintenance of normal blood glucose levels through diet and insulin administration. Biessels, G. J. and Van Dam, P. S., *Neurosci. Res. Commun.,* 1997, 20, 1–10.

A considerable body of evidence now suggests that deficiencies in the levels of certain proteinaceous growth factors, or neurotrophic factors, may play key pathoetiological roles in both peripheral and central neurodegenerative diseases. Tomlinson, D. R., Fernyhough, P. and Diemel, L. T. *Diabetes,* 1997, 46(suppl. 2) S43–S49; Hamilton, G. S., *Chem. Ind., (London)* 1998, 4,127–132; Louvel, E., Hugon, J. and Doble, A., *Trends Pharmacol. Sci.,* 1997, 18, 196–203; Ebadi, M., et al., *Neurochem. Int.,* 1997, 30, 347–374.

These neurotrophic factors can be divided into two structural classes: (1) the neurotrophins, including nerve growth factor ("NGF"), glial cell-derived neurotrophic growth factor ("GDNF"), brain-derived neurotrophic factor ("BDNF"), neurotrophin 3 ("NT-3"), neurotrophin 4/5 ("NT-4/5"), and neurotrophin 2 ("NT-2"); and (2) ciliary neurotrophic factor ("CNTF") which is related to the cytokine family of molecules. All neurotrophic factors promote neurite outgrowth, induce differentiation, and suppress programmed cell death or apoptosis in specific subpopulations of peripheral and central neurons. For example, NGF exerts trophic effects on sympathetic and sensory neurons of the dorsal root ganglion and cholinergic neurons of medial septum in the CNS, suggesting potential therapeutic utility in AD. CNTF has trophic actions on a broad cross-section of neurons, including parasympathetic, sensory, sympathetic, motor, cerebellar, hippocampal, and septal neurons. Of particular interest is the fact that CNTF partially prevents the atrophy of skeletal muscle following nerve lesioning but has no effect on innervated muscle, indicating that CNTF is primarily operative in the pathological state. As a result, CNTF is currently being evaluated for its effects in musculoskeletal diseases like ALS.

The clinical utility of proteinaceous neurotrophic agents is severely hampered by their limited bioavailability, especially in the CNS. This necessitates the administration of these agents directly into the brain to induce a therapeutic effect—a relatively hazardous and cumbersome route of administration.

Chemical Agents

U.S. Pat. No. 5,294,603 to Rinehart discloses several didemnin derivatives in which proline in position 8 is replaced with L-azetidine-2-carboxylic acid. These synthetic didemnin derivatives are described as exhibiting antiviral, cytotoxic and immunosuppressive activities. Among the intermediates in the synthesis of these analogs are compounds wherein R is hydrogen or benzyl, having the following general structure:

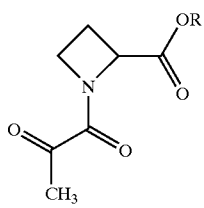

Lyons, W. E., et al. (*Proc. Natl. Acad. Sci.*, 1994, 91(8), 3191–5) describe the neurotrophic effects of the immunosuppressant drug FK506, which shows neurotrophic activity in cultures of PC12 cells and sensory ganglia:

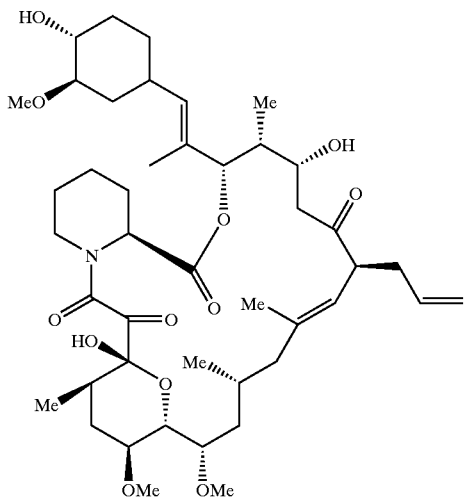

Vertex Pharmaceuticals, Inc. ("Vertex") in a South African Application 964852, discloses compounds that are described as useful for inhibiting the rotamase activity of the FKBP12 immunophilin and stimulating neurite outgrowth in cell cultures. These compounds are typified by the following structure:

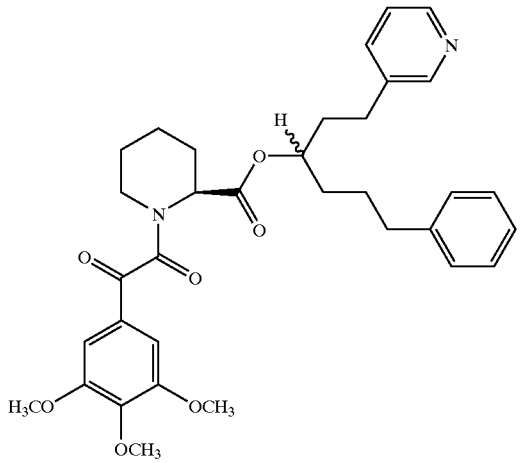

Vertex PCT Application WO 92/19593 discloses a series of compounds that are described as useful for inhibiting the rotamase activity of FK506-binding proteins ("FKBP") and inhibiting T cell activation. These compounds are exemplified by the following structure:

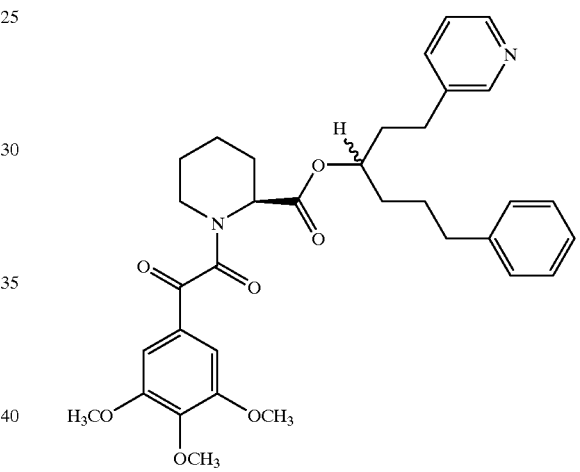

Vertex PCT Application WO 94/07858 discloses a series of compounds that are described as useful multi-drug-resistant cancer cell-sensitizers for maintaining, increasing or restoring the sensitivity of cells to therapeutic or prophylactic agents. The compounds are exemplified by the following structure:

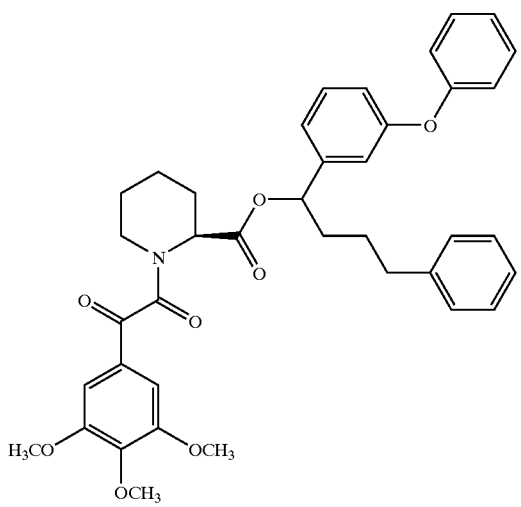

Patents collectively to Guilford Pharmaceuticals, Inc., GPI NIL Holdings, Inc. and Johns Hopkins University School of Medicine (collectively "Guilford") disclose compounds that are described as useful for inhibiting the activity of FKBP-type immunophilins, stimulating neuronal growth and regeneration, and treating neurological disorders.

In particular, Guilford U.S. Pat. No. 5,696,135 and PCT application WO 96/40140 disclose a method of using pipecolic acid derivative compounds, related to FK506 and rapamycin, to treat a neurological disorder in an animal. The compounds therein are described as useful for inhibiting the rotamase activity of an FKBP-type immunophilin, stimulating neuronal growth in chick dorsal root ganglion in vitro, and promoting repair of lesioned sciatic nerves in rats.

Guilford U.S. Pat. No. 5,798,355 discloses a method of using macrocyclic and acyclic pipecolic acid derivatives, which it describes as inhibiting the enzyme activity of FKBP-type immunophilins and stimulating neuronal growth and regeneration.

Guilford U.S. Pat. Nos. 5,614,547 and 5,795,908, and PCT application WO 96/40633, disclose a series of N-glyoxyl-prolyl ester compounds that are described as useful for inhibiting the rotamase activity of the FKBP-12 immunophilin, promoting neuronal growth and regeneration, and treating neurological disorders. The compounds are typified by the following structure:

Guilford U.S. Pat. No. 5,801,197 and PCT application WO 97/16190 disclose a series of nonimmunosuppressive pipecolic acid derivatives that are described as useful for the treatment of damaged nerves in animals. The following are representative analogs of the series:

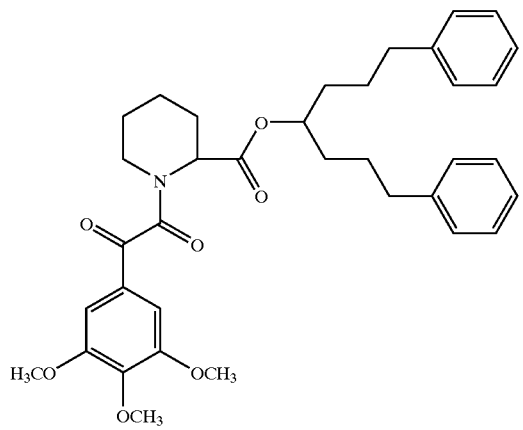

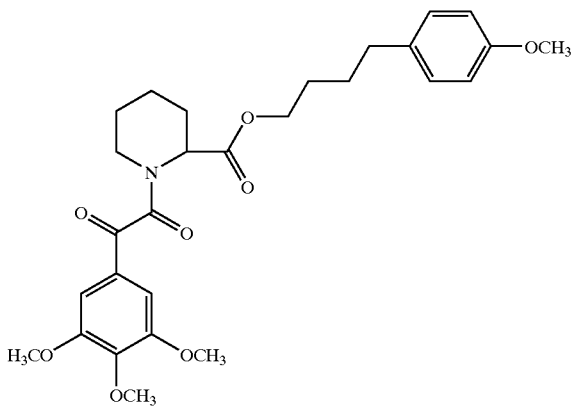

Guilford U.S. Pat. No. 5,721,256 discloses compounds that are described as useful for inhibiting the rotamase activity of FKBP, promoting neuronal growth and regeneration, and effecting neuronal activity in an animal. The series of sulfonamide compounds are typified by the following structure:

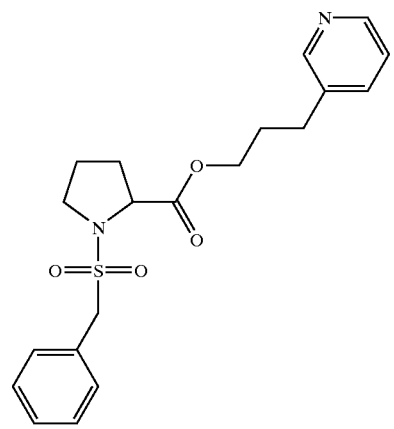

Guilford U.S. Pat. No. 5,801,187 and PCT application WO 98/13355 disclose a series of heterocyclic ester and amide compounds that are described as useful for inhibiting the rotamase activity of FKBP, promoting neuronal growth and regeneration, and effecting neuronal activity in an animal. The compounds are typified by the following structure:

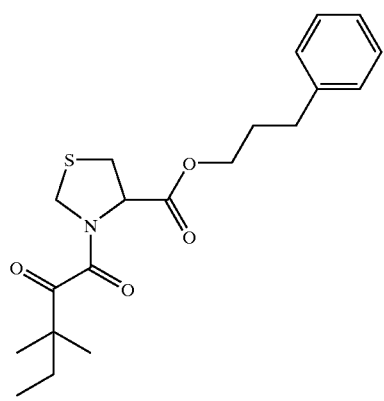

Guilford PCT Application WO 98/13343 discloses a series of heterocyclic thioester and ketone compounds that are described as useful for inhibiting the rotamase activity of FKBP, promoting neuronal growth and regeneration, and effecting neuronal activity in an animal. The compounds are exemplified by the following structure:

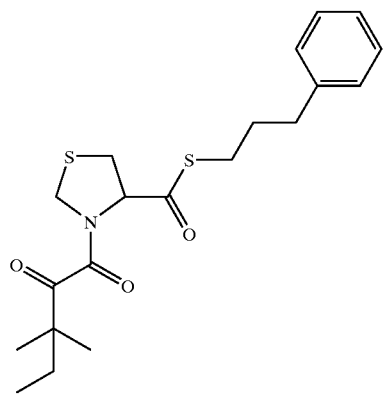

Guilford PCT Application WO 98/29116 discloses a series of N-linked sulfonamide compounds of heterocyclic thioesters that are described as useful for inhibiting the rotamase activity of FKBP, promoting neuronal growth and regeneration, and effecting neuronal activity in an animal. The compounds are typified by the following structure:

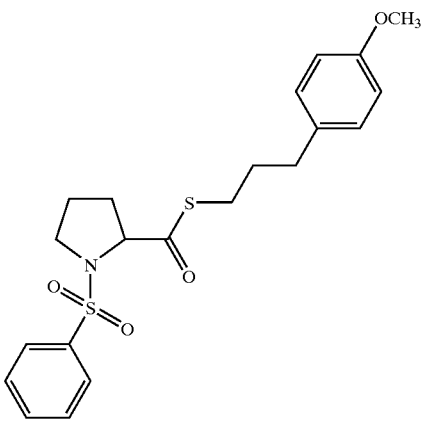

Guilford PCT Application WO 98/29117 discloses a series of N-linked ureas and carbamate compounds of heterocyclic thioesters that are described as useful for inhibiting the rotamase activity of FKBP, promoting neuronal growth and regeneration, and effecting neuronal activity in an animal. The compounds are typified by the following structure:

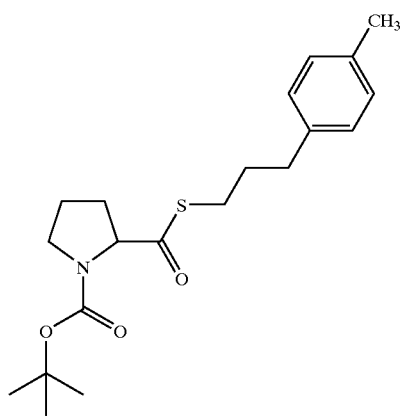

Guilford PCT Application WO 98/37882 discloses a method of using small molecule carbamate and urea compounds that are described as useful for inhibiting the rotamase activity of FKBP-type immunophilins and stimulating neuronal growth and regeneration. The compounds are typified by the following structure:

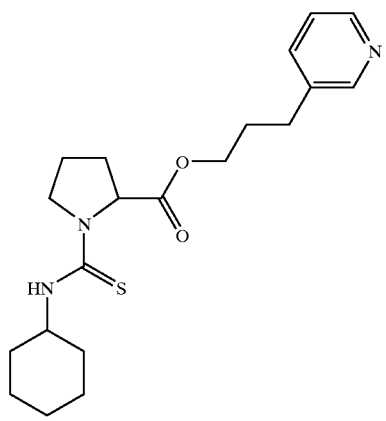

Guilford PCT Application WO 98/37885 discloses a series of N-oxide compounds of heterocyclic esters, amides, thioesters and ketones that are described as useful for inhibiting the rotamase activity of FKBP, promoting neuronal growth and regeneration and treating neurological disorders in an animal. The compounds are typified by the following structure:

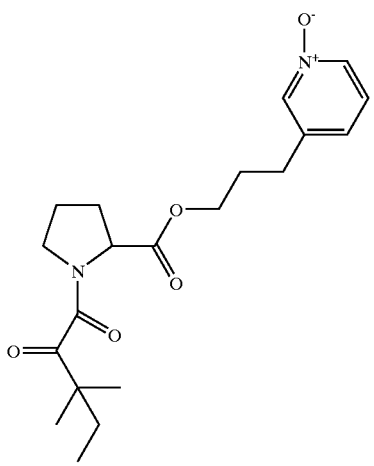

Guilford PCT Application WO 98/25950 discloses a series of tetra- and pentapeptide compounds containing at least two proline residues, which compounds are described as useful for inhibiting the rotamase activity of cyclophilin, promoting neuronal growth and regeneration, and effecting neuronal activity in an animal.

None of the known agents discussed herein has ever been demonstrated as having therapeutic or prophylactic efficacy against neurodegenerative disorders in humans. Thus, there exists a strong and unmet need for agents having such efficacy.

SUMMARY OF THE INVENTION

This invention provides a compound having the structure:

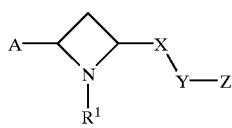

or a pharmaceutically acceptable salt thereof, wherein (a) $R^1$ is selected from the group consisting of:
  (i) $COCOR^2$, wherein $R^2$ is $(C_1-C_6)$-straight or branched alkyl, $(C_1-C_6)$-straight or branched alkenyl, $(C_5-C_7)$cycloalkyl, 2-thienyl, 3-thienyl, phenyl, or substituted phenyl (the substituted phenyl ring having one to three substituents independently selected from the group consisting of lower alkyl, lower alkoxy, hydroxy and halogen),
  (ii) $CONHR^3$, wherein $R^3$ is $(C_1-C_6)$-straight or branched alkyl,
  (iii) $SO_2R^4$, wherein $R^4$ is phenylalkyl or substituted phenylalkyl (the substituted phenyl ring having one to three substituents independently selected from the group consisting of lower alkyl, lower alkoxy, hydroxy and halogen), and
  (iv)

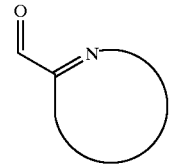

wherein the ring portion thereof is aromatic and optionally contains one or more heteroatoms selected from the group consisting of oxygen, sulfur and nitrogen;

(b) X and Y are (i) C=O and (ii) O or $NR^5$ (wherein $R^5$ is $(C_1-C_6)$-straight or branched alkyl), respectively, or alternatively together form a 1,5-disubstituted tetrazole ring;

(c) Z is $(C_1-C_5)$-straight or branched alkyl or alkenyl substituted in one or more positions with Ar, which Ar is selected from the group consisting of 2-pyridyl, 3-pyridyl, 4-pyridyl, phenyl and substituted phenyl (the substituted phenyl ring having from one to three substituents independently selected from the group consisting of lower alkyl, lower alkoxy, hydroxy and halogen), with the proviso that Z and $R^2$ cannot both be $C_1$-alkyl; and (d) A is X—Y—Z or hydrogen.

This invention also provides a method of stimulating neuronal growth comprising contacting neurons with an effective amount of the instant compound. This invention further provides a pharmaceutical composition comprising one of the instant compounds and a pharmaceutically acceptable carrier.

This invention still further provides a method of treating a subject afflicted with a disorder characterized by neuronal damage caused by disease or trauma, comprising administering to the subject a therapeutically effective amount of the instant pharmaceutical composition. Finally, this invention provides a method of inhibiting in a subject the onset of a disorder characterized by neuronal damage caused by disease, comprising administering to the subject a prophylactically effective amount of the instant pharmaceutical composition.

BRIEF DESCRIPTION OF THE FIGURE

FIG. 1 shows the in vivo biological activity of instant Compound 1 using the rat facial nerve compression model. In this model, compressing the facial nerve causes paralysis of the whisker muscle on that side of the face. The untreated facial nerve on the other side functions as an internal control. Treatment with Compound 1 demonstrated that whisker movement on the paralyzed side was restored more rapidly compared to treatment with a vehicle and the internal control. The whisker movement recovery rate on the paralyzed side compared to the vehicle and internal control is shown in this FIGURE.

DETAILED DESCRIPTION OF THE INVENTION

This invention provides novel 2-azetidinecarboxylic acid derivatives having surprising neurotrophic activity. These compounds, along with related pharmaceutical compositions and methods, are useful in the treatment and prevention of neuronal disorders such as Parkinson's disease, Alzheimer's disease, stroke, multiple sclerosis, amyotrophic lateral sclerosis, diabetic neuropathy and Bell's palsy.

Specifically, this invention provides a compound having the structure:

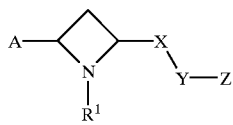

or a pharmaceutically acceptable salt thereof, wherein
(a) $R^1$ is selected from the group consisting of:
  (i) $COCOR^2$, wherein $R^2$ is $(C_1-C_6)$-straight or branched alkyl, $(C_1-C_6)$-straight or branched alkenyl, $(C_5-C_7)$-cycloalkyl, 2-thienyl, 3-thienyl, phenyl, or substituted phenyl (the substituted phenyl ring having one to three substituents independently selected from the group consisting of lower alkyl, lower alkoxy, hydroxy and halogen),
  (ii) $CONHR^3$, wherein $R^3$ is $(C_1-C_6)$-straight or branched alkyl,
  (iii) $SO_2R^4$, wherein $R^4$ is phenylalkyl or substituted phenylalkyl (the substituted phenyl ring having one to three substituents independently selected from the group consisting of lower alkyl, lower alkoxy, hydroxy and halogen), and
  (iv)

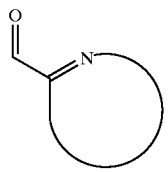

wherein the ring portion thereof is aromatic and optionally contains one or more heteroatoms selected from the group consisting of oxygen, sulfur and nitrogen;
(b) X and Y are (i) C=O and (ii) O or $NR^5$ (wherein $R^5$ is $(C_1-C_6)$-straight or branched alkyl), respectively, or alternatively together form a 1,5-disubstituted tetrazole ring;
(c) Z is $(C_1-C_5)$-straight or branched alkyl or alkenyl substituted in one or more positions with Ar, which Ar is selected from the group consisting of 2-pyridyl, 3-pyridyl, 4-pyridyl, phenyl and substituted phenyl (the substituted phenyl ring having from one to three substituents independently selected from the group consisting of lower alkyl, lower alkoxy, hydroxy and halogen), with the proviso that Z and $R^2$ cannot both be $C_1$-alkyl; and
(d) A is X—Y—Z or hydrogen.

In one embodiment of this compound, Z is $C_3$-straight alkyl substituted in one or more positions with 3-pyridyl. In another embodiment, $R^1$ is $COCOR^2$, $R^2$ being $C_5$-branched alkyl. In the preferred embodiment, the instant compound is selected from the group consisting of instant Compounds 1, 2, 3, 7, 8, 10, 13, 14, 15 and 18.

The instant compounds can be isolated and used as free bases. They can also be isolated and used as pharmaceutically acceptable salts. Examples of such salts include hydrobromic, hydroiodic, hydrochloric, perchloric, sulfuric, maleic, fumaric, malic, tartaric, citric, benzoic, mandelic, methanesulfonic, hydroethanesulfonic, benzenesulfonic, oxalic, palmoic, 2-naphthalenesulfonic, p-toluenesulfonic, cyclohexanesulfamic and saccharic.

This invention also provides a method of stimulating neuronal growth comprising contacting neurons with an effective amount of the instant compound. The contacting can be performed, for example, in vitro, ex vivo or in vivo.

This invention further provides a pharmaceutical composition comprising the instant compound and a pharmaceutically acceptable carrier.

Pharmaceutically acceptable carriers are well known to those skilled in the art and include, but are not limited to, from about 0.01 to about 0.1 M and preferably 0.05 M phosphate buffer or 0.8% saline. Such pharmaceutically acceptable carriers can be aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, ethanol, alcoholic/aqueous solutions, glycerol, emulsions or suspensions, including saline and buffered media. Oral carriers can be elixirs, syrups, capsules, tablets and the like. The typical solid carrier is an inert substance such as lactose, starch, glucose, methyl-cellulose, magnesium stearate, dicalcium phosphate, mannitol and the like. Parenteral carriers include sodium chloride solution, Ringers dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like. All carriers can be mixed as needed with disintegrants, diluents, granulating agents, lubricants, binders and the like using conventional techniques known in the art.

This invention further provides a method of treating a subject afflicted with a disorder characterized by neuronal damage caused by disease or trauma, comprising administering to the subject a therapeutically effective amount of the instant pharmaceutical composition.

As used herein, the term "subject" includes, without limitation, any animal or artificially modified animal. In the preferred embodiment, the subject is a human.

Administering the instant pharmaceutical composition can be effected or performed using any of the various methods known to those skilled in the art. The instant compounds can be administered, for example, intravenously, intramuscularly, orally, subcutaneously, and directly into the cerebrospinal fluid and/or brain. In the preferred embodiment, the instant pharmaceutical composition is administered orally. Additionally, administration can comprise giving the subject a plurality of dosages over a suitable period of time. Such administration regimens can be determined according to routine methods.

Disorders characterized by neuronal damage are numerous and include the following, without limitation: Alzheimer's disease, Pick's disease, diffuse Lewy body disease, progressive supranuclear palsy (Steel-Richardson syndrome), multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohifart-Kugelberg-Welander disease, spastic paraparesis, progressive multifocal leukoencephalopathy, and prion diseases (including Creutzfeldt-Jakob, Gerstmann-Sträussler-Scheinker disease, Kuru and fatal familial insomnia).

Other disorders include, without limitation, diffuse white matter disease (Binswanger's disease), head trauma and diffuse brain damage, spinal cord injury, intracranial and intravertebral lesions (including, but not limited to, contusion, penetration, shear, compression and laceration), stroke resulting from cerebral ischemia or infarction, embolic occlusion and thrombotic occluocclusion, and intracranial hemorrhage of any type (including, but not limited to, epidural, subdural, subarachnoid and intracerebral).

Further disorders include, without limitation, demyelinating diseases such as multiple sclerosis; polyradiculoneuritis (Guillain-Barré syndrome); subacute demyelinating polyneuropathies; brain lesions induced by acute disseminated encephalomyelitis, acute hemorrhagic leukoencephalitis or systemic lupus erythematosus; Behçet's syndrome associated with multifocal brain lesions, neuropathy and/or myelopathy; sarcoidosis associated with nerve damage or atrophy or myelopathy; bacterial or viral infections resulting in brain, spinal cord, nerve damage, meningoradiculitis, and/or myelopathy; subacute combined degeneration; transverse myelitis; Leber's hereditary neuropathy; subacute necrotic encephalopathy (Leigh's disease); mitochondrial encephalopathy with demyelination; metachromatic leukodystrophy; Krabbe's disease; Fabry's disease; adrenoleukodystrophy; neuromyelitis optica (Devic's syndrome); demyelinating Schwannopathies; cranial and peripheral neuropathies including, but not limited to, Déjerine-Sottas neuropathy and its variants; Charcot-Marie-Tooth disease and its variants; hereditary polyneuropathies; sensory and motor neuropathies; axonal neuropathies; adrenomyeloneuropathy; Refsum's disease; neuropathies due to porphyria, acute or chronic toxins/drugs intoxications with either axonal, demyelinating, sensory, motor and/or autonomic involvement; Friedreich's ataxia; ataxia-telangiectasia; and metachromatic leukodystrophy; chronic neuropathies, including, but not limited to, diabetes mellitus and other metabolic dysregulations and dysproteinemias (metabolic neuropathies including those due to alcoholism); and inflammatory/immunological processes (inflammatory neuropathies, herpes zoster-associated neuropathy, and leprous neuritis).

Further disorders include, without limitation, the traumatic neuropathies of the peripheral or cranial nerves, Bell's palsy and other facial nerve neuropathies, trigeminal neuropathy, vestibular neuropathy, accessory nerve neuropathy, vagal neuropathy, glossopharyngeal neuropathy, optic nerve neuropathy, oculomotor nerve neuropathy, multiple cranial nerves palsies, plexopathies, root disorders, idiopathic brachial neuritis, plexitis, multifocal neuropathy, and autonomic nervous system neuropathies.

In one embodiment of this invention, the disorder treated is caused by disease, and is selected from the group consisting of Parkinson's disease, Alzheimer's disease, stroke, multiple sclerosis, amyotrophic lateral sclerosis, diabetic neuropathy and Bell's palsy. In another embodiment, the disorder treated is caused by trauma to the brain, spinal cord or peripheral nerves.

This invention still further provides a method of inhibiting in a subject the onset of a disorder characterized by neuronal damage caused by disease, comprising administering to the subject a prophylactically effective amount of the instant pharmaceutical composition.

In one embodiment, the disorder inhibited is selected from the group consisting of Parkinson's disease, Alzheimer's disease, stroke, multiple sclerosis, amyotrophic lateral sclerosis, diabetic neuropathy and Bell's palsy.

As used herein, a "therapeutically effective dose" of a pharmaceutical composition is an amount sufficient to stop, reverse or reduce the progression of a disorder. A "prophylactically effective dose" of a pharmaceutical composition is an amount sufficient to inhibit the onset of a disorder, i.e., eliminate, ameliorate and/or delay the disorders onset. Methods are known in the art for determining therapeutically and prophylactically effective doses for the instant pharmaceutical composition. The effective dose for administering the pharmaceutical composition to a human, for example, can be determined mathematically from the results of animal studies.

In one embodiment, the therapeutically and/or prophylactically effective dose is a dose sufficient to deliver from about 0.01 mg/kg to about 200 mg/kg of body weight of the instant compound. In another embodiment, the therapeutically and/or prophylactically effective dose is a dose sufficient to deliver from about 0.1 mg/kg to about 50 mg/kg. In the preferred embodiment, the therapeutically and/or prophylactically effective dose is a dose sufficient to deliver from about 1 mg/kg to about 30 mg/kg.

This invention will be better understood by reference to the Experimental Details which follow, but those skilled in the art will readily appreciate that these are only illustrative of the invention as described more fully in the claims which follow thereafter. Additionally, throughout this application, various publications are cited. The disclosure of these publications is hereby incorporated by reference into this application to describe more fully the state of the art to which this invention pertains.

EXPERIMENTAL DETAILS

I. General Synthetic Methods

Representative compounds of the present invention can be synthesized in accordance with the general synthetic methods described below and illustrated in the following schemes. In these schemes, Arabic and Roman numerals are used interchangeably to refer to various compounds. Compounds referred to in this section by Arabic numerals are not to be confused with the specific compounds referred to by Arabic numerals in Table 1 and elsewhere herein.

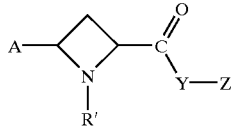
I

[wherein A and Z are as used herein, R' is $COCOR^2$, $CONHR^3$, $SO_2R^4$,

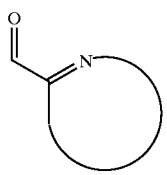

or benzyloxycarbonyl, $R^2$, $R^3$, and $R^4$ are as described previously, Y is O or $NR^5$ and $R^5$ is as described previously] can be prepared by reaction of Compound 2, of the general formula:

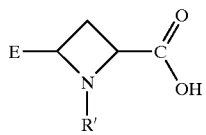
II

[wherein R' is $COCOR^2$, $CONHR^3$, $SO_2R^4$,

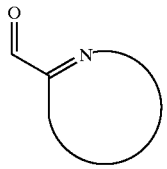

or benzyloxycarbonyl, $R^2$, $R^3$ and $R^4$ are as described previously and E is hydrogen or $CO_2H$], with an appropriately substituted alcohol or amine in the presence of a coupling agent such as diisopropylcarbodiimide, dicyclohexylcarbodiimide, 1-ethyl-3-(3'-dimethylaminopropyl)carbodiimide hydrochloride (EDCI), benzotriazol-1-yloxytris(dimethylamino)phosphonium hexafluorophosphate (BOP; Castro's reagent) or bromo-tris-pyrrolidinophosphonium hexafluorophosphate (PyBroP) in an inert solvent, such as tetrahydrofuran, dimethylformamide or methylene chloride at temperatures ranging from about 0° C. to about 370° C. for about 2 to about 48 hours. Frequently, an additive such as hydroxybenzotriazole (HOBt) or 7-azahydroxybenzotriazole (HOAt) is added to suppress racemization during the reaction. Condensations performed with phosphonium (BOP, PyBroP) or uronium salts (HBTU, TBTU, HATU) are conducted with a carboxylate salt as one of the coupling partners. Therefore, an organic amine base, such as diisopropylethylamine, triethylamine, or N-methylmorpholine is generally added. Particularly in the case of condensations performed with a carbodiimide, an acylation catalyst, such as camphorsulfonic acid or dimethylaminopyridine, also may be added. It is understood that in the case of (I) where A is

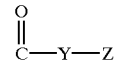

and E is $CO_2H$, at least two equivalents of the amine or alcohol and two equivalents of the coupling agent must be employed to effect the desired transformation.

Scheme 2

Alternatively, Compound 1 [wherein R' is $COCOR^2$ or benzyloxycarbonyl, $R^2$ and Z are as described previously, A is hydrogen, Y is O or $NR^5$ and $R^5$ is as described previously] can be prepared by reaction of Compound 3, of the general formula:

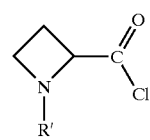
III

[wherein R' is $COCOR^2$ or benzyloxycarbonyl and $R^2$ is as described previously] with an appropriate amine or alcohol in the presence of an organic tertiary amine base, such as diisopropylethylamine, N-methylmorpholine, or triethylamine. The reaction is generally conducted in an inert solvent such as dichloromethane, chloroform, tetrahydrofuran, or dioxane, at temperatures ranging from about −20° C. to about 37° C. for about 2 to about 48 hours.

Scheme 3

Compound 3 [wherein R' is $COCOR^2$ or benzyloxycarbonyl and $R^2$ is as described previously] can be prepared by reaction of Compound 2 [wherein R' is $COCOR^2$ or benzyloxycarbonyl, $R^2$ is as described previously and E is hydrogen] with a suitable chlorinating agent, such as oxalyl chloride or thionyl chloride, generally in the presence of a catalyst, like dimethylformamide. The reaction is generally conducted in an inert solvent such as dichloromethane, chloroform, tetrahydrofuran, dioxane, or benzene at temperatures ranging from about 0° C. to about 80° C. for about 2 to about 24 hours.

Scheme 4

Alternatively, Compound 1 [wherein R' is $COCOR^2$, $CONHR^3$, $SO_2R^4$, or

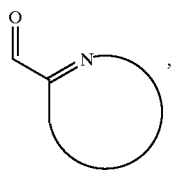
,

Y is O, Z is as described previously and A is hydrogen or

can also be prepared by the transesterification of Compound 4, of the general formula:

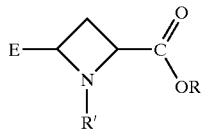
IV

[wherein R' is COCOR², CONHR³, SO₂R⁴ or

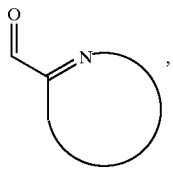

E is hydrogen or CO₂R and R is lower alkyl] with an appropriate alcohol in the presence of a catalytic amount of titanium tetraisopropoxide. The reaction can be run neat or in an inert solvent, such as toluene or benzene, at temperatures ranging from about room temperature to about 110° C. for about 2 to about 48 hours.

Scheme 5

Compound 2 [wherein R' is COCOR², CONHR³, SO₂R⁴,

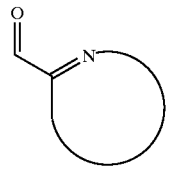

or benzyloxycarbonyl and E is hydrogen or CO₂H] can also be prepared by reaction of Compound 4 [wherein R' is COCOR², CONHR³, SO₂R⁴,

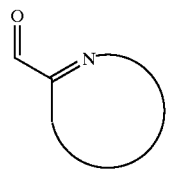

or benzyloxycarbonyl, E is hydrogen or CO₂R and R is lower alkyl] with an alkali metal hydroxide or alkali metal carbonate such as lithium hydroxide, sodium hydroxide, or potassium carbonate in a mixed aqueous solvent system such as tetrahydrofuran/water or methanol/water at temperatures ranging from about 0° C. to about 60° C. for 2 about to about 48 hours.

Scheme 6

Compound 5, of the general formula:

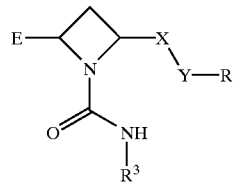
V

[wherein R³ is as described previously, E is hydrogen or X—Y—R. wherein X is C=O, Y is O, or X and Y together form a 1,5-disubstituted tetrazole ring, and R is (C₁–C₅)-straight or branched alkyl or alkenyl, optionally substituted in one or more positions with Ar (wherein Ar is selected from the group consisting of 2-pyridyl, 3-pyridyl, 4-pyridyl and phenyl, the phenyl ring having one to three substituents which are independently selected from the group consisting of hydrogen, lower alkyl, lower alkoxy, hydroxy and halogen)] can be prepared by condensation of Compound 6, of the general formula:

VI

[wherein E is hydrogen or X—Y—R, wherein X is C=O, Y is O, or X and Y together form a 1,5-disubstituted tetrazole ring, and R is (C₁–C₅)-straight or branched alkyl or alkenyl, optionally substituted in one or more positions with Ar (wherein Ar is selected from the group consisting of 2-pyridyl, 3-pyridyl, 4-pyridyl and phenyl, the phenyl ring having one to three substituents which are independently selected from the group consisting of hydrogen, lower alkyl, lower alkoxy, hydroxy and halogen)] with a alkyl isocyanate in an inert solvent, such as dichloromethane, chloroform, ether, tetrahydrofuran, or dioxane. The reaction may be conducted at temperatures ranging from about 0° C. to about 60° C. for about 2 to about 48 hours.

Scheme 7

Compound 7, of the general formula:

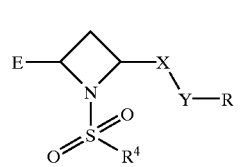
VII

[wherein R⁴ is as described previously, E is hydrogen or X—Y—R, wherein X is C=O, Y is O, or X and Y together form a 1,5-disubstituted tetrazole ring, and R is (C₁–C₅)-straight or branched alkyl or alkenyl, optionally substituted in one or more positions with Ar (wherein Ar is selected from the group consisting of 2-pyridyl, 3-pyridyl, 4-pyridyl and phenyl, the phenyl ring having one to three substituents which are independently selected from the group consisting of hydrogen, lower alkyl, lower alkoxy, hydroxy, and halogen)] can be prepared by reaction of Compound 6 [wherein E is hydrogen or X—Y—R, wherein X is C=O, Y is O, or X and Y together form a 1,5-disubstituted tetrazole ring, and R is ($C_1$–$C_5$)-straight or branched alkyl or alkenyl, optionally substituted in one or more positions with Ar (wherein Ar is selected from the group consisting of 2-pyridyl, 3-pyridyl, 4-pyridyl and phenyl, the phenyl ring having one to three substituents which are independently selected from the group consisting of hydrogen, lower alkyl, lower alkoxy, hydroxy and halogen)] with a suitably substituted sulfonyl chloride in an inert solvent, such as dichloromethane, chloroform, ether, tetrahydrofuran, or dioxane in the presence of an organic tertiary amine base, like triethylamine, diisopropylethylamine, N-methylmorpholine. The reaction may be conducted from about 0° C. to about 100° C. for about 2 to about 48 hours.

Scheme 8

Compound 8, of the general formula:

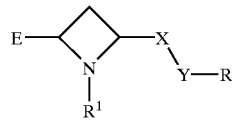

VIII

[wherein $R^1$ is COCOR$^2$ or

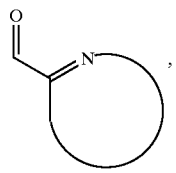

$R^2$ is as described previously, E is hydrogen or X—Y—R, wherein X is C=O, Y is O, or X and Y together form a 1,5-disubstituted tetrazole ring and R is ($C_{1-5}$)-straight or branched alkyl or alkenyl, optionally substituted in one or more positions with Ar (wherein Ar is selected from the group consisting of 2-pyridyl, 3-pyridyl, 4-pyridyl and phenyl, the phenyl ring having one to three substituents which are independently selected from the group consisting of hydrogen, lower alkyl, lower alkoxy, hydroxy and halogen)] can be prepared by reaction of Compound 6 [wherein E is hydrogen or X—Y—R, wherein R is lower alkyl, X is C=O, Y is O, or X and Y together form a 1,5-disubstituted tetrazole ring, and R is ($C_{1-5}$)-straight or branched alkyl or alkenyl, optionally substituted in one or more positions with Ar (wherein Ar is selected from the group consisting of 2-pyridyl, 3-pyridyl, 4-pyridyl and phenyl, the phenyl ring having one to three substituents which are independently selected from the group consisting of hydrogen, lower alkyl, lower alkoxy, hydroxy and halogen)] with a suitably substituted carboxylic acid derivative in the presence of a coupling agent such as diisopropylcarbodiimide, dicyclohexylcarbodiimide, 1-ethyl-3-(3'-dimethylaminopropyl)carbodiimide hydrochloride (EDCI), benzotriazol-1-yloxytris(dimethylamino)phosphonium hexafluorophosphate (BOP; Castro's reagent) or bromo-tris-pyrrolidinophosphonium hexafluorophosphate (PyBroP) in an inert solvent, such as tetrahydrofuran, dimethylformamide or methylene chloride at temperatures ranging from about 0° C. to about 37° C. for about 2 to about 48 hours.

Condensations performed with phosphonium (BOP, PyBroP) or uronium salts (HBTU, TBTU, HATU) are conducted with a carboxylate salt as one of the coupling partners. Therefore, an organic amine base, such as diisopropylethylamine, triethylamine, or N-methylmorpholine, is generally added. Particularly in the case of condensations performed with a carbodiimide, an acylation catalyst, such as camphorsulfonic acid or dimethylaminopyridine also may be added.

Scheme 9

Compound 9, of the general formula:

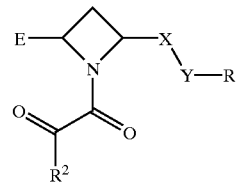

IX

[wherein $R^2$ is as described previously, E is hydrogen or X—Y—R, wherein X is C=O, Y is O, or X and Y together form a 1,5-disubstituted tetrazole ring, and R is ($C_1$–$C_5$)-straight or branched alkyl or alkenyl, optionally substituted in one or more positions with Ar (wherein Ar is selected from the group consisting of 2-pyridyl, 3-pyridyl, 4-pyridyl and phenyl, the phenyl ring having one to three substituents which are independently selected from the group consisting of hydrogen, lower alkyl, lower alkoxy, hydroxy and halogen)] can be prepared by reaction of Compound 10, of the general formula:

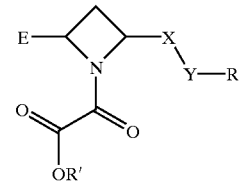

X

[wherein E is hydrogen or X—Y—R, wherein X is C=O, Y is O, or X and Y together form a 1,5-disubstituted tetrazole ring, and R is ($C_{1-5}$)-straight or branched alkyl or alkenyl, optionally substituted in one or more positions with Ar (wherein Ar is selected from the group consisting of 2-pyridyl, 3-pyridyl, 4-pyridyl and phenyl, the phenyl ring having one to three substituents which are independently selected from the group consisting of hydrogen, lower alkyl, lower alkoxy, hydroxy and halogen), and R' is lower alkyl] with a suitably protected Grignard reagent in an inert solvent such as tetrahydrofuran or diethyl ether at temperatures ranging from about –78° C. to about 0° C. for about 2 to about 24 hours depending on the reactivity of the oxamate.

Scheme 10

Compound 10 [wherein E is hydrogen or X—Y—R, wherein X is C=O, Y is O, or X and Y together form a 1,5-disubstituted tetrazole ring, and R is ($C_1$–$C_5$)-straight or branched alkyl or alkenyl, optionally substituted in one or more positions with Ar (wherein Ar is selected from the group consisting of 2-pyridyl, 3-pyridyl, 4-pyridyl and phenyl, the phenyl ring having one to three substituents which are independently selected from the group consisting of hydrogen, lower alkyl, lower alkoxy, hydroxy and halogen), and R' is lower alkyl] can be prepared by reaction of Compound 6 [wherein E is hydrogen or X—Y—R, wherein X is C=O, Y is O, or X and Y together form a 1,5-disubstituted tetrazole ring, and R is ($C_1$–$C_5$)-straight or branched alkyl or alkenyl, optionally substituted in one or more positions with Ar (wherein Ar is selected from the group consisting of 2-pyridyl, 3-pyridyl, 4-pyridyl and phenyl, the phenyl ring having one to three substituents which are independently selected from the group consisting of hydrogen, lower alkyl, lower alkoxy, hydroxy and halogen)] with an alkyl oxalyl chloride in an inert solvent such as methylene chloride for about 2 to about 24 hours. Generally, the reaction is conducted in the presence of an organic tertiary amine such as diisopropylethylamine or triethylamine from about 0° C. to about 37° C.

Scheme 11

Alternatively, Compound 6 [wherein E is hydrogen or $CO_2R$, R is lower alkyl, X is C=O, and Y is O] can be prepared by reaction of Compound 11, of the general formula:

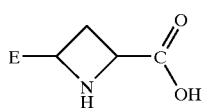

XI

[wherein E is hydrogen or $CO_2H$] with a lower alkanol in the presence of an acid catalyst such as hydrogen chloride or p-toluenesulfonic acid. Alternatively, thionyl choride, sulfuryl chloride or acetyl chloride may be added to the lower alkanol in the presence of Compound 11 to effect the desired conversion. The aminoester product is generally isolated as the hydrochloride salt.

Scheme 12

In another alternative, Compound 6 [wherein E is hydrogen or X—Y—R, X is C=O, Y is O, or X and Y together form a 1,5-disubstituted tetrazole ring, and R is ($C_1$–$C_5$)-straight or branched alkyl or alkenyl, which is substituted in one or more positions with Ar (wherein Ar is selected from the group consisting of 2-pyridyl, 3-pyridyl, 4-pyridyl and phenyl, the phenyl ring having one to three substituents which are independently selected from the group consisting of hydrogen, lower alkyl, lower alkoxy, hydroxy and halogen)] can be prepared by reaction of Compound 12, of the general formula:

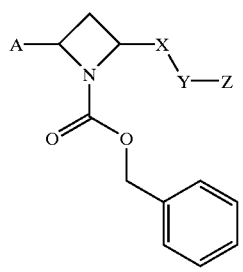

XII

[wherein A is as previously described, X is C=O, Y is O, or X and Y together form a 1,5-disubstituted tetrazole ring, and Z is as previously described] by standard methods for removal of the N-benzyloxycarbonyl group. Such methods include catalytic hydrogenation over a noble metal catalyst like palladium on carbon in an alcoholic solvent for about 4 to about 24 hours generally at about room temperature, by reaction with boron tribromide in an inert solvent like methylene chloride for about 2 to about 6 hours at temperatures ranging from about 0° C. to about 25° C., or by reaction with a strong acid like hydrobromic acid in acetic acid for about 2 to about 6 hours at temperatures ranging from about 20° C. to about 100° C.

Scheme 13

Compound 13, of the general formula:

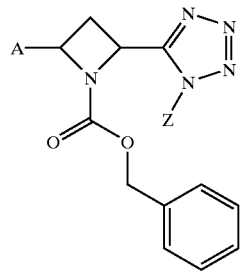

XIII

[wherein A is hydrogen or

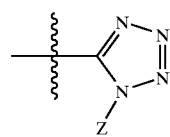

and Z is as previously described] can be prepared by reaction of Compound 1 [wherein Z is as described previously, A is hydrogen or

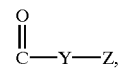

wherein Y is NH and R' is benzyloxycarbonyl] with hydrazoic acid, sodium azide or trimethylsilylazide. The reaction is effected through the intermediacy of an imidoyl chloride or imidoyl sulfonate by adding a reagent such as phosphorus pentachloride, phosphorus oxychloride or trifluoromethanesulfonic anhydride optionally in the presence of a base, such as pyridine in an inert solvent like dichloromethane, 1,2-dichloroethane or acetonitrile. The reaction is generally conducted at temperatures ranging from about 0° C. to about 37° C. for about 3 to about 48 hours.

Scheme 14

Compound 14, of the general formula:

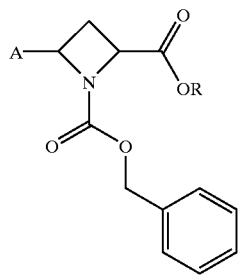

[wherein A is hydrogen or CO$_2$R and R is lower alkyl] can be prepared by reaction of Compound 6 [wherein E is hydrogen or CO$_2$R, X is C=O, Y is O, and R is lower alkyl] with benzyl chloroformate in the presence of an organic or inorganic base, such as diisopropylethylamine or sodium hydroxide. Generally, the reaction is conducted in an inert solvent, such as dichloromethane or tetrahydrofuran. However, when an inorganic base is employed, the reaction may be conducted in water or water/organic solvent mixtures. The reaction may be run at temperatures ranging from about 0° C. to about 37° C. for about 2 to about 24 hours.

The alcohols and amines used in the synthesis of Compound 1, the carboxylic acid derivatives used in the synthesis of Compound 8, the sulfonyl chlorides used in the preparation of Compound 7, the isocyanates used in the synthesis of Compound 5, and the Grignard reagents used in the preparation of Compound 9, Compound 6 [wherein E is X—Y—R, wherein X is C=O, Y is O, and R is lower alkyl] and Compound 11 [wherein E is hydrogen or CO$_2$H] when not commercially available, can be obtained by known procedures using readily accessible starting materials using standard reagents and reaction conditions (see, for example, Hoshino, J., Hiraoka, J., Hata, Y., Sawada, S., Yamamoto, Y. *J. Chem. Soc., Perkin Trans.* 1 1995, 6, 693–697; Moehrle, H., Specks, F. *Arch. Pharm.* (*Weinheim, Ger.*) 1975, 308, 23–33; Hawes, E. M., Davis, H. L. *J. Het. Chem.* 1973, 10, 39–42).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

II. Selected Compounds of the Invention

In the preferred embodiment of this invention, the instant compound is selected from the group of compounds shown in Table 1 below.

TABLE 1

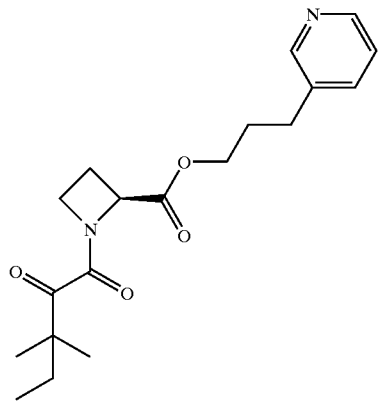

1

Compound 1

TABLE 1-continued
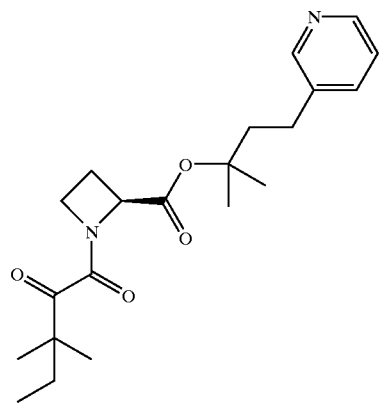
2
Compound 2
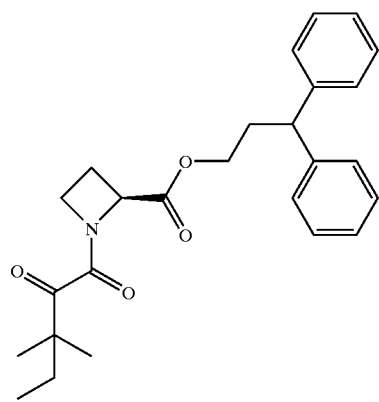
3
Compound 3
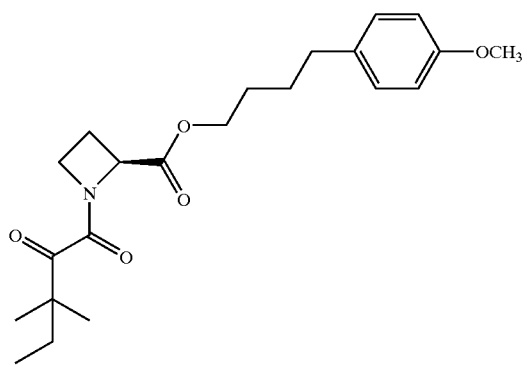
4
Compound 4

TABLE 1-continued
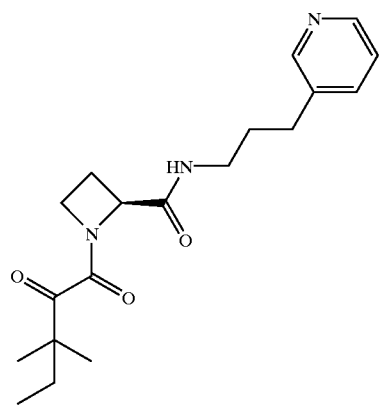
5
Compound 5
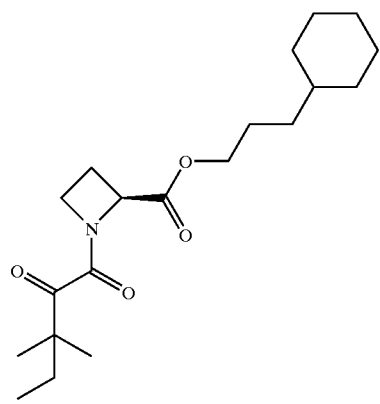
6
Compound 6
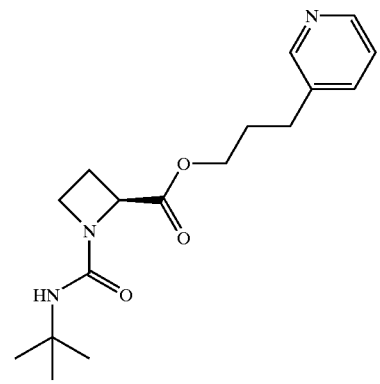
7
Compound 7

TABLE 1-continued
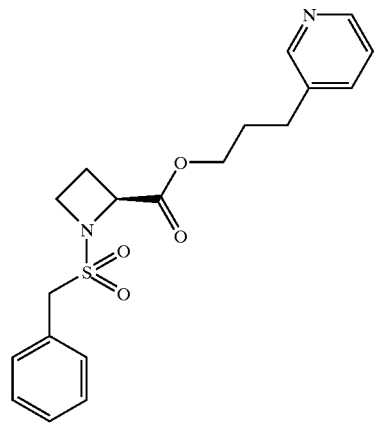
8
Compound 8
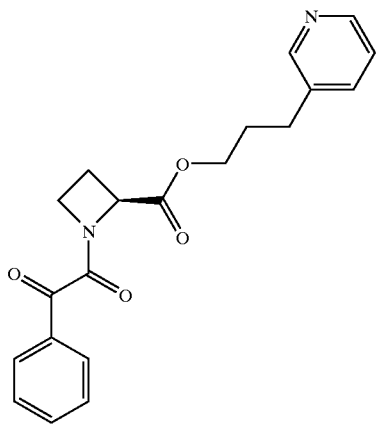
9
Compound 9
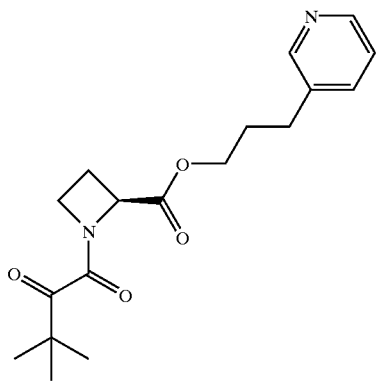
10
Compound 10

TABLE 1-continued
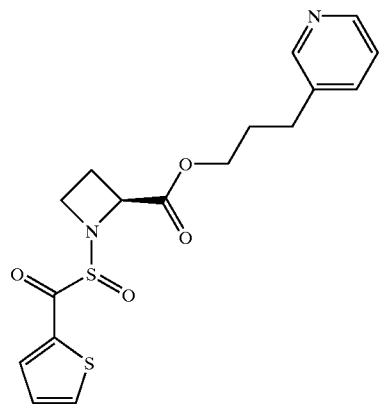
11
Compound 11
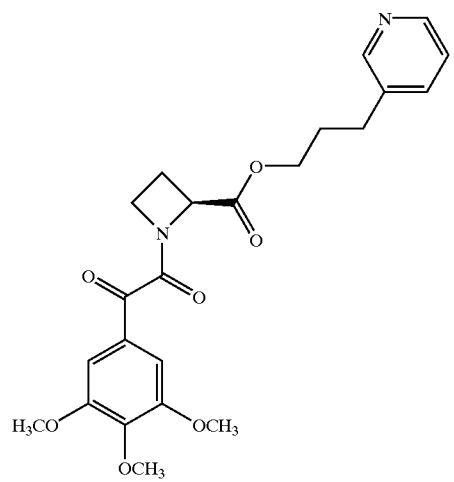
12
Compound 12
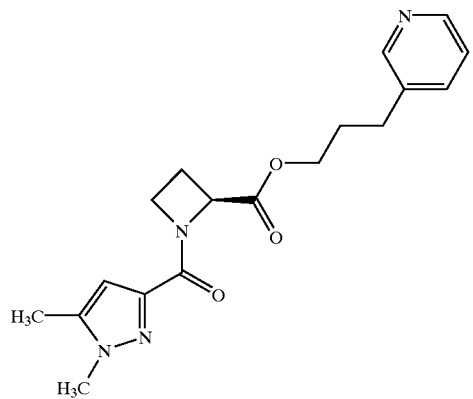
13
Compound 13

TABLE 1-continued
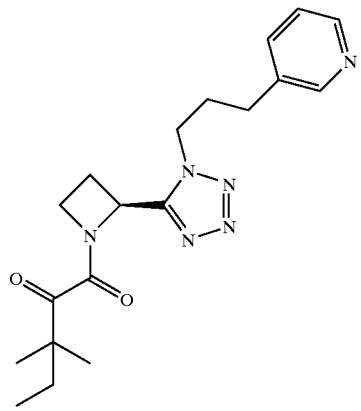
14
Compound 14
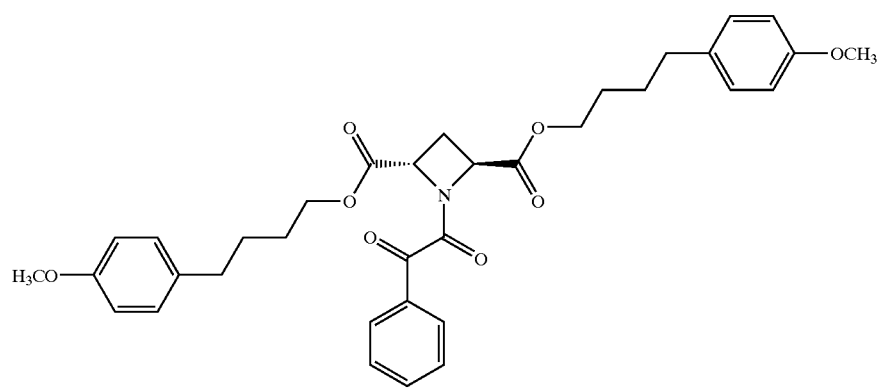
15
Compound 15
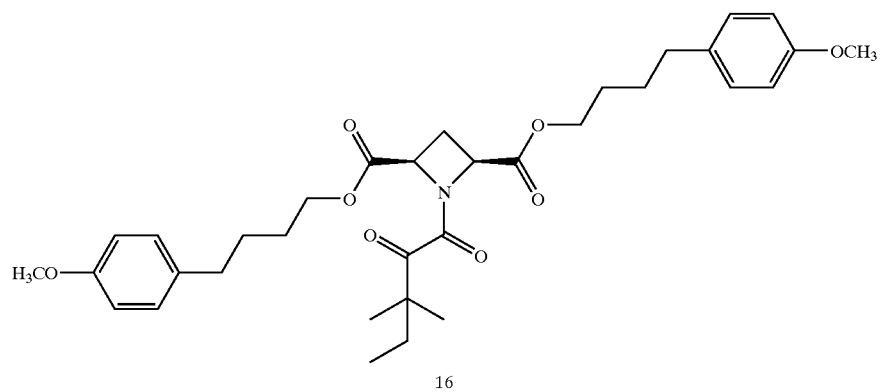
16
Compound 16

TABLE 1-continued
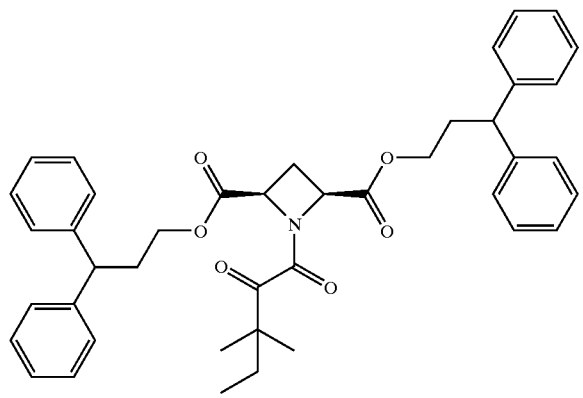
Compound 17
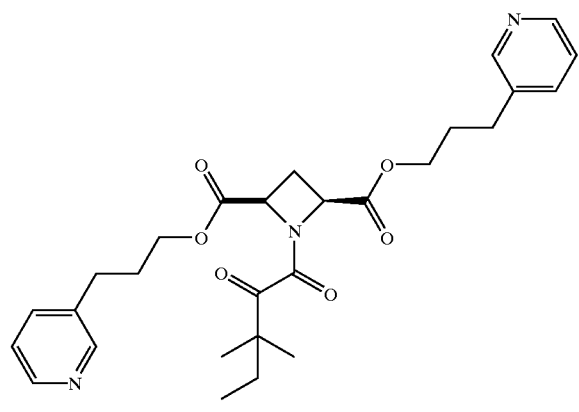
Compound 18
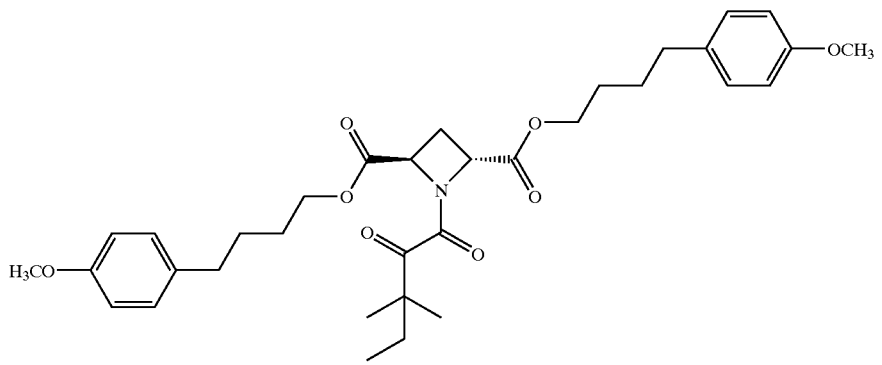
Compound 19

TABLE 1-continued

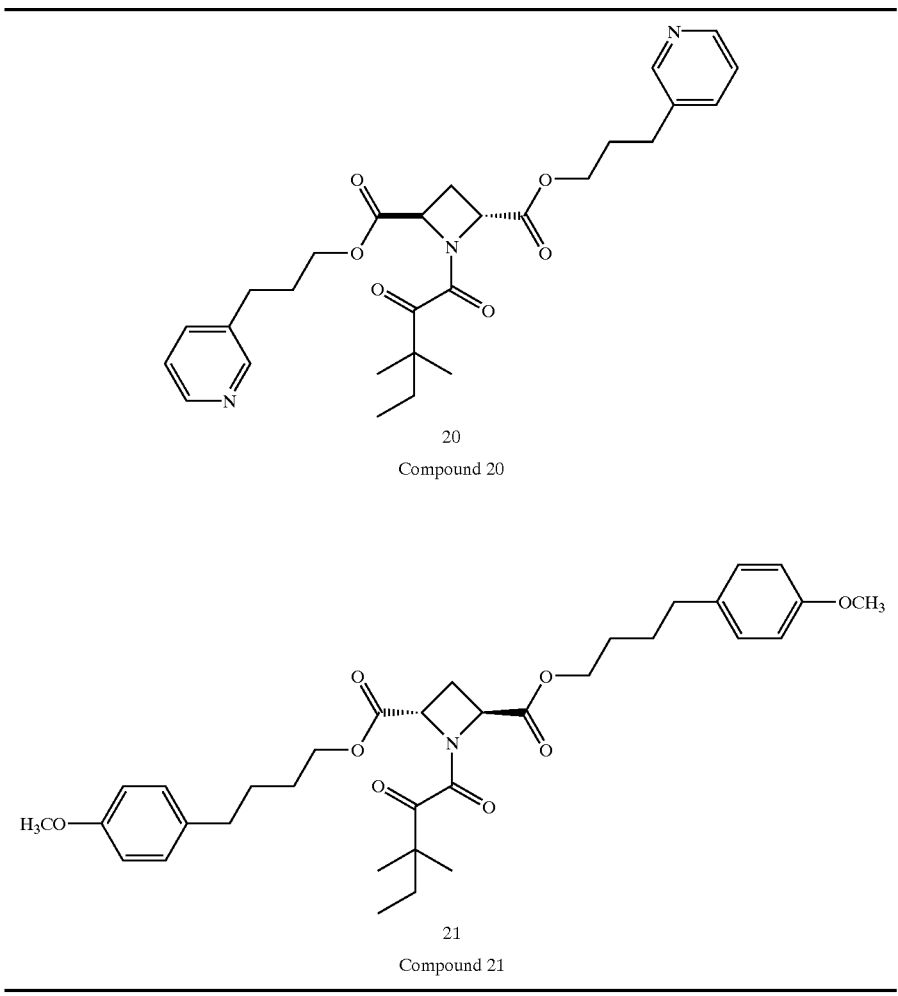

Compound 20

Compound 21

III. Specific Synthetic Methods

Specific compounds which are representative of this invention can be prepared as per the following examples. For the sake of clarity, compounds of the invention produced in the following examples are identified by the term "Compound" followed by the appropriate numeral (e.g., "Compound 1"). Intermediates in the synthesis of compounds of the invention are designated as "Reference Examples." No attempt has been made to optimize the yields obtained in these reactions. One skilled in the art would know how to increase such yields through routine variations in reaction times, temperatures, solvents and/or reagents.

The products of some Reference Examples may be used as intermediates to produce more than one of the instant compounds. In those cases, the choice of intermediates to be used to produce subsequent compounds of the present invention is a matter of discretion that is well within the capabilities of those skilled in the art.

Reference Example 1

(2S)-Methyl azetidine-2-carboxylate hydrochloride (2S)-Methyl-1-azetidine-2-carboxylic acid (1.23 g, 12.2 mmol, 1.0 eq) was suspended in methanol (25 mL) and cooled to about 0° C. After dropwise addition of thionyl chloride over about 20 minutes, the mixture was stirred at room temperature for 3 hours and then the solvent was removed in vacuo, maintaining the temperature below about 50° C. The residue was triturated with ether several times and dried under vacuum below about 50° C. to give 1.85 g of Reference Example 1 as a yellow oil (quantitative yield). $^1$H NMR (CDCl$_3$) δ 2.64–2.95 (br, 2H); 3.88 (s, 3H); 4.03–4.16 (br, 2H); 5.11–5.30 (br, 1H); 9.46–9.68 and 10.10–10.37(br,1H).

Reference Example 2

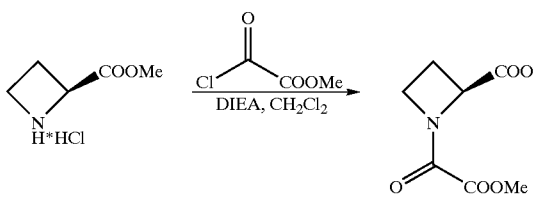

(2S)-Methyl-1-(1,2-dioxo-2-methoxyethyl)azetidine-2-carboxylate (2S)-Methyl azetidine-2-carboxylate from Reference Example 1 (1.83 g, 12.09 mmol, 1.0 eq) was dissolved in dry dichloromethane (25 mL) and cooled to about 0° C. under an argon atmosphere. After adding methyl oxalyl chloride (1.16 mL, 12.11 mmol, 1.0 eq), N,N-diisopropylethylamine (4.30 mL, 24.69 mmol, 2.0 eq) was added dropwise to the mixture. The reaction mixture was stirred at about 0° C. for about 30 minutes and then at about room temperature for about 2 hours. The solvent was evaporated and the residue triturated with a mixture of ether and dichloromethane (1:1). The triturant was concentrated and the residue subjected to flash chromatography (ether) to give 1.00 g (41% yield) of Reference Example 2 as a colorless oil. $^1$H NMR (CDCl$_3$) δ 2.24–2.40 (m, 1H); 2.43–2.84 (m, 1H); 3.80, 3.83, 3.87 and 3.92 (4s, 6H); 4.09–4.69 (series of m, 2H); 4.83 and 5.29 (dd, 1H, J=9.4, 6.9).

Reference Example 3

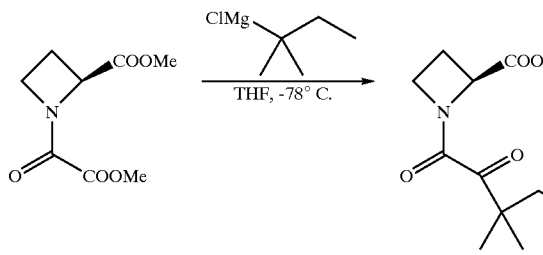

(2S)-Methyl-1-(1,2-dioxo-3,3-dimethylpentyl)azetidine-2-carboxylate

To a cooled (about −78° C.) solution of (2S)-Methyl-1-(1,2-dioxo-2-methoxyethyl)-azetidine-2-carboxylate from Reference Example 2 (0.98 g, 4.86 mmol, 1.0 eq) in dry tetrahydrofuran (15 mL) under an argon atmosphere was added 1,1-dimethylpropylmagnesium chloride in THF (6.30 mL of 1M solution, 6.30 mmol, 1.3 eq) over about 15 minutes. After stirring the resulting homogeneous mixture at about −78° C. for about 3 hours, the mixture was poured into chilled saturated ammonium chloride and extracted into ethyl acetate (2×50 mL). The organic phase was washed with water, dried over sodium sulfate and concentrated. Flash chromatography of the residue (2:3 ether:pentane) produced 0.90 g (77% yield) of the product as a colorless oil. $^1$H NMR (CDCl$_3$) δ 0.77–0.98 (m, 3H); 1.20–1.30 (series of s, 6H); 1.68–2.01 (m, 2H); 2.24–2.40 (m, 1H); 2.60–2.80 (m, 1H); 3.80–3.82 (series of s, 3H); 3.99–4.43 (series of m, 2H); 4.84 and 5.26 (series of dd, 1H, J=6.9, 9.4).

Reference Example 4

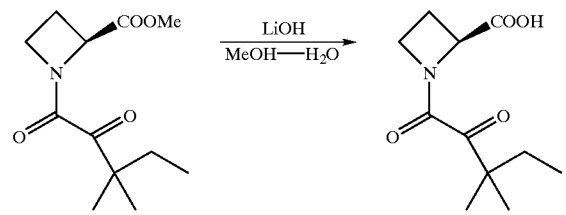

(2S)-1-(1,2-Dioxo-3,3-dimethylpentyl)azetidine-2-carboxylic acid

To a solution of (2S)-Methyl-1-(1,2-dioxo-3,3-dimethylpentyl)-azetidine-2-carboxylate from Reference Example 3 (0.64 g, 2.65 mmol) in a 1:1 mixture of ether-:methanol (20.0 mL) was added LiOH in water (4.9 mL, 1N solution) at about 0° C. The mixture was stirred at about 0° C. for about 30 minutes and then at about room temperature overnight. The pH was adjusted to about pH 1 by adding 1N HCl, then the mixture was diluted with water and extracted with dichloromethane. The organic layers were washed with brine and dried over sodium sulfate and then concentrated to give 0.40 g (67% yield) of the product as a yellow semisolid. $^1$H NMR (DMSO) δ 0.77–0.83 (m, 3H); 1.20–1.29 (series of s, 6H); 1.49–2.84 (series of m, 4H); 4.02–4.43 (series of m, 2H); 5.01–5.31 (series of dd, 1H); 6.10–6.80 (br, 1H).

Compound 1

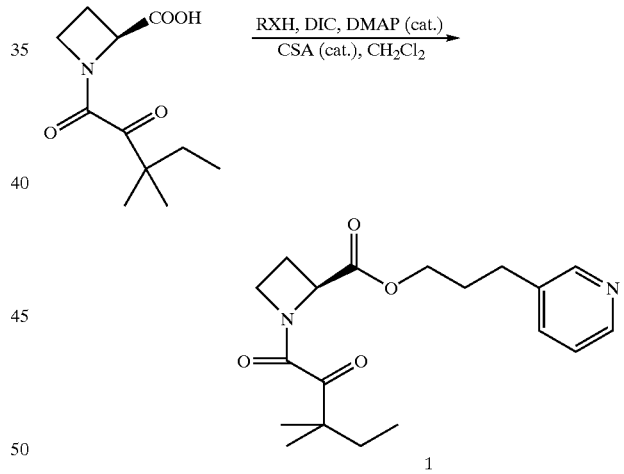

1

(2S)-[3-(3-Pyridyl)1-propyl]-1-(1,2-dioxo-3,3-dimethylpentyl)azetidine-2-carboxylate A mixture of (2S)-1-(1,2-dioxo-3,3-dimethylpentyl)-azetidine-2-dicarboxylic acid from Reference Compound 4 (349.1 mg, 1.54 mmol, 1.0 eq), 3-(3-pyridyl)-1-propanol (195 μL, 1.51 mmol, 0.98 eq), diisopropylcarbodiimide (385 μL, 2.46 mmol, 1.60 eq), camphorsulfonic acid (119.6 mg, 0.51 mmol, 0.33 eq) and dimethylaminopyridine (66.4 mg, 0.54 mmol, 0.35 eq) in dry dichloromethane (10 mL) was stirred at about room temperature for about thirty hours under argon. The solid was filtered off and washed with dichloromethane. The organic filtrate was concentrated and the residue subjected to flash chromatography (1:20 methanol:chloroform) to give 319.2 mg (60% yield) of the product as a yellow oil which solidified on standing. $^1$H NMR (CDCl$_3$) δ 0.77–0.88 (series of t, 3H); 1.21–1.27 (series of s, 6H); 1.69–2.78 (series of m, 8H); 3.98–4.42 (series of m, 4H); 4.82 and 5.22 (dd, 1H, J=9.4, 6.9); 7.20–7.27 (m,1H); 7.52 (dd, 1H, J=7.7); 8.47 (br s, 2H).

Compound 2

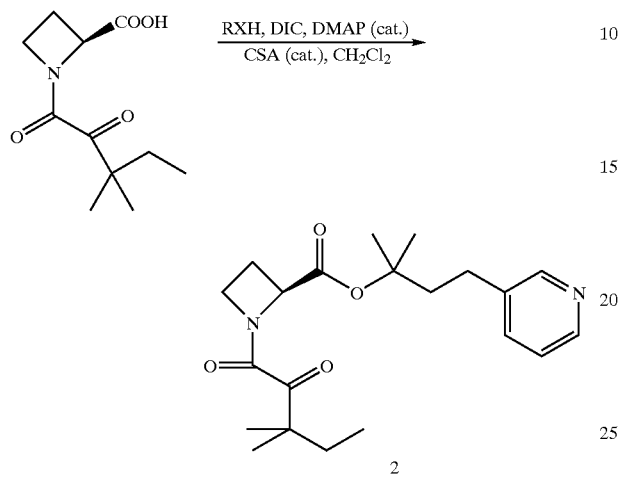

2

(2S)-[3-(3-Pyridyl)-1,1-dimethyl-1-propyl]-1-(1,2-dioxo-3,3-dimethylpentyl)azetidine-2-dicarboxylate The title compound was prepared as described for Compound 1 except that 2-methyl-4-(3-pyridyl)butan-2-ol was used in place of 3-(3-pyridyl-1-propanol (76% yield). $^1$H NMR (CDCl$_3$): δ 0.77–0.89 (m, 3H); 1.11–1.69 (series of s, 12H); 1.69–2.78 (series of m, 8H); 3.82–4.48 (series of m, 2H); 4.70 and 5.13 (dd, 1H, J=9.4, 6.9); 7.18–7.27 (m, 1H); 7.49–7.59 (m, 1H); 8.42–8.51 (m, 2H).

Compound 3

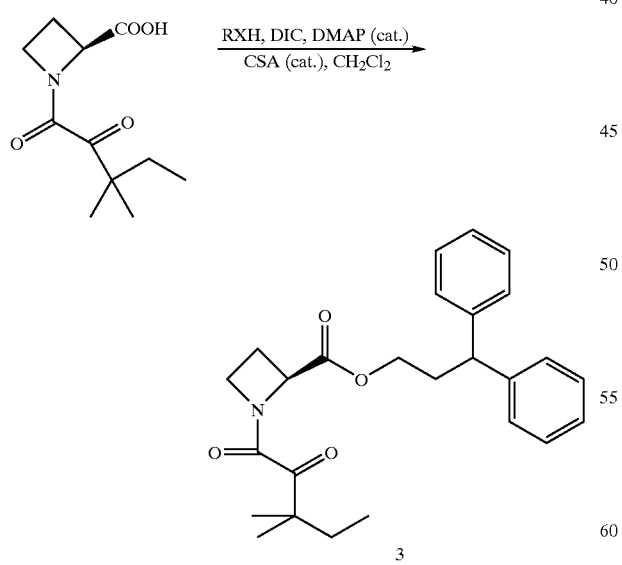

3

(2S)-(3,3-Diphenyl-1-propyl)1-(1,2-dioxo-3,3-dimethylpentyl) azetidine-2-carboxylate The title compound was prepared as described for Compound 1 except that 3,3-diphenylpropan-1-ol was used in place of 3-(3-pyridyl)-1-propanol (55% yield). $^1$H NMR (CDCl$_3$) δ 0.77–0.88 (m, 3H); 1.18–1.29 (series of s, 6H); 1.68–2.76 (series of m, 6H); 3.98–4.37 (series of m, 5H); 4.80 and 5.21 (dd, 1H, J=9.4, 6.9); 7.16–7.36 (m, 10H).

Compound 4

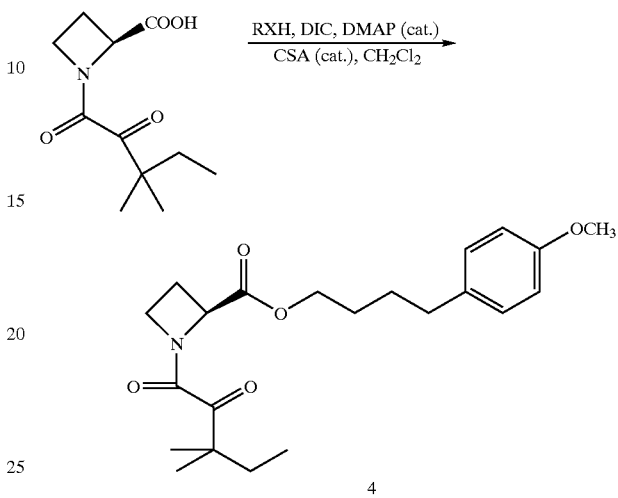

4

(2S)-[4-(4-Methoxyphenyl)-1-butyl]-1-(1,2-dioxo-3,3-dimethylpentyl)azetidine-2-carboxylate The title compound was prepared as described for Compound 1 except that 4-(4-methoxyphenyl)butan-1-ol was used in place of 3-(3-pyridyl1-propanol (49% yield). $^1$H NMR (CDCl$_3$) δ 0.77–0.94 (series of t, 3H); 1.18–1.29 (series of s, 6H); 1.60–2.78 (series of m, 10H); 3.78 (s, 3H); 3.98–4.40 (series of m, 4H); 4.80 and 5.21 (dd, 1H, J=9.4, 6.9); 6.83 (d, 2H, J=8.6); 7.11 (d, 2H, J=8.6).

Compound 5

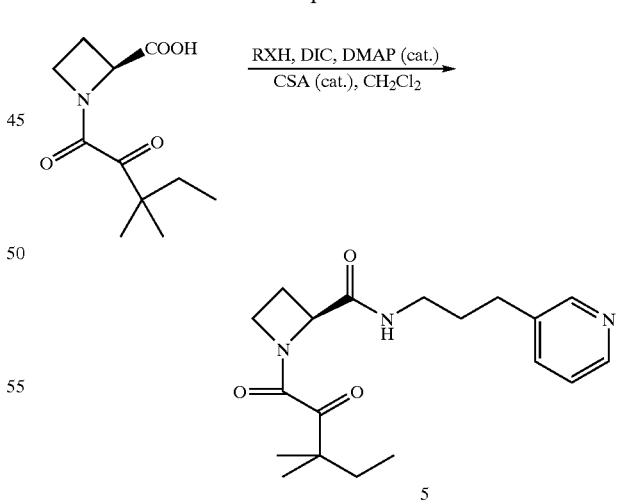

5

1-(1,2-Dioxo-3,3-dimethylpentyl)-(2S)-N-[3-(3-pyridyl)-1-propyl]azetidine-2-carboxamide The title compound was prepared as described for Compound 1 except that 3-(3-pyridyl)-1-propylamine was used in place of 3-(3-pyridyl)1-propanol (2% yield). $^1$H NMR (CDCl₃) δ 0.82 (t, 3H, J=8.6); 1.20 (s, 6H); 1.74–2.82 (series of m, 8H); 3.28–3.40 (m, 2H); 4.17–4.30 (m, 2H); 4.96 (dd, 1H, J=9.4, 6.9); 7.19–7.26 (m,1H); 7.53 (d,1H J=7.7); 7.65 (br s,1H); 8.46 (s, 2H).

Compound 6

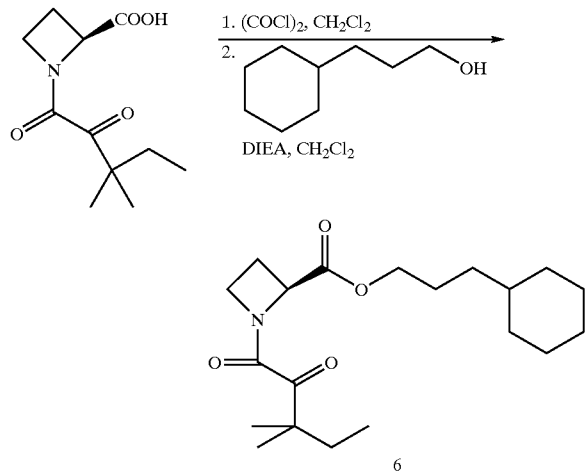

(2S)-(3-Cyclohexyl-1-propyl)-1-(1,2-dioxo-3,3-dimethylpentyl)azetidine-2-carboxylate (2S)-1-(1,2-Dioxo-3,3-dimethylpentyl)azetidine-2-dicarboxylic acid from Reference Compound 4 (343.0 mg, 1.51 mmol, 1.0 eq) was dissolved in dry dichloromethane (5 mL) and cooled to about 0° C. under argon. Oxalyl chloride (190 μL, 2.18 mmol, 1.4 eq) and two drops of DMF were added to the solution. The mixture was warmed to reflux temperature with stirring over about 3 hours. After cooling, the mixture was concentrated and used as such in the next step.

The crude acid chloride was dissolved in dry dichloromethane (10 mL) to which was added diisopropylethylamine (350 μL, 2.0 mmol, 1.3 eq) and then 3-cyclohexyl-1-propanol (250 μL, 1.7 mmol, 1.1 eq) at about 0° C. under argon. The mixture was stirred at about room temperature overnight and diluted with ether (30 mL). The organic solution was washed by 1N HCl (3×10 mL), then dried over magnesium sulfate and concentrated. The residue was subjected to flash chromatography (1:1 ether:pentane) to give 339.2 mg (64% yield for two steps) of the product as a slightly yellow oil. ¹H NMR (CDCl₃) δ 0.78–1.98 (series of m and s, 26H); 2.21–2.35 (m, 1H); 2.59–2.77 (m, 1H); 3.58–4.37 (series of m, 4H); 4.59 and 5.21 (dd, 1H, J=9.4, 6.9).

Reference Example 5

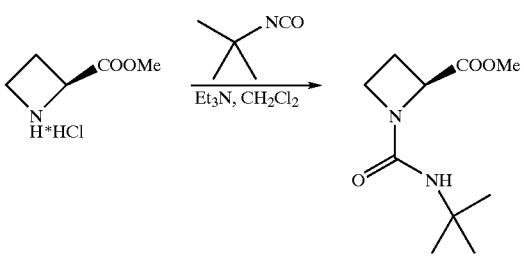

(2S)-Methyl-1-(N-t-butylcarbamoyl)azetidine-2-carboxylate (2S)-Methyl azetidine-2-carboxylate hydrochloride from Reference Example 1 (185.8 mg, 1.23 mmol, 1.0 eq) was dissolved in dry dichloromethane (10.0 mL) and treated with t-butyl isocyanate (210 μL, 1.84 mmol, 1.5 eq) at about 0° C. under an argon atmosphere. After adding triethylamine (190 μL, 1.36 mmol, 1.1 eq) dropwise, the reaction mixture was warmed to about room temperature and stirred overnight. The solvent was evaporated and the residue was subjected to flash chromatography (1:1 ether:dichloromethane) to give 211.6 mg (80% yield) of the product as a colorless oil. ¹H NMR (CDCl₃) δ 1.33 (s, 9H); 2.34–2.49 (m, 2H); 3.66–3.76 (m, 1H); 3.80 (s, 3H); 3.90 (q, 1H, J=8.6); 4.61 (t, 1H, J=8.6); 5.07–5.16 (br, 1H).

Reference Example 6

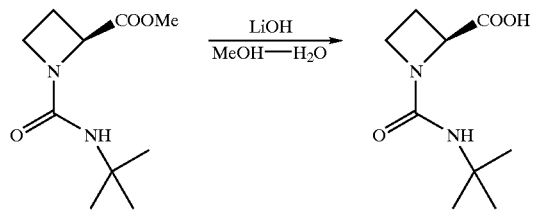

(2S)-1-(N-t-butylcarbamoyl)azetidine-2-carboxylic acid

To a solution of (2S)-methyl-1-(N-t-butylcarbamoyl) azetidine-2-carboxylate from Reference Example 5 (211.6 mg, 0.99 mmol) in methanol (5.0 mL) was added 1N LiOH in water (1.8 mL) at about 0° C. The mixture was warmed to about room temperature and stirred under argon overnight. The pH was adjusted to about pH 1 by adding 1N HCl and then the mixture was diluted with water and extracted with ethyl acetate. The organic layer was dried over magnesium sulfate and concentrated to give 211.3 mg (85% yield) of the product as a yellow oil. ¹H NMR (CDCl₃) δ 1.38 (s, 9H); 2.34–2.46 (m, 1H); 2.61–2.74 (m, 1H) 3.71–3.88 (m, 2H); 4.18–4.26 (br, 1H); 4.82 (t, 1H, J=8.6).

Compound 7

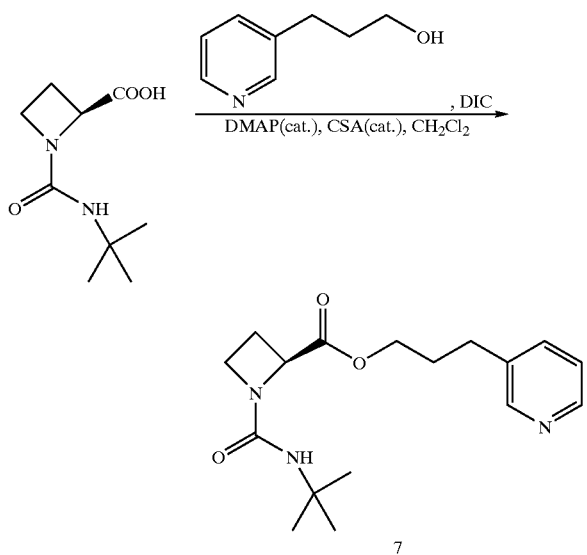

(2S)-[3-(3-Pyridyl-1-propyl]-1-(N-t-butylcarbamoyl)
azetidine-2-carboxylate

A mixture of (2S)-1-(N4-butylcarbamoyl)-azetidine-2-carboxylic acid from Reference Example 6 (192.8 mg, 0.96 mmol, 1.0 eq), 3-(3-pyridyl)-1-propanol (130 μL, 1.01 mmol, 1.0 eq), diisopropylcarbodiimide (220 μL, 1.41 mmol, 1.40 eq), camphorsulfonic acid (85 mg, 0.37 mmol, 0.33 eq) and dimethylaminopyridine (42 mg, 0.34 mmol, 0.35 eq) in dry dichloromethane (6 mL) was stirred at about room temperature for abut 15 hours under argon. The suspended solid was filtered off and washed with dichloromethane. The organic filtrate was concentrated and the residue subjected to flash chromatography (1:20 methanol:chloroform) to give 141.2 mg (46% yield) of the product as a yellow oil. $^1$H NMR (CDCl$_3$) δ 1.35 (s, 9H); 1.96–2.10 (m, 2H); 2.33–2.47 (m, 2H); 2.73 (t, 2H, J=7.7); 3.70–3.79 (m, 1H); 3.92 (q,$_1$H, J=8.6); 4.18–4.30 (m, 2H); 4.61 (t, 1H, J=8.6); 5.01–5.09 (br,$_1$H); 7.20–7.28 (m, 1H); 7.52 (m,1H); 8.44–8.50 (br, 2H).

Reference Example 7

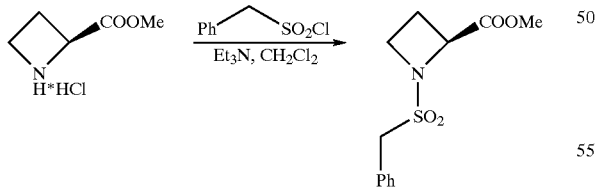

(2S)-Methyl-1-(α-toluenesulfonyl)azetidine-2-carboxylate (2S)-Methyl azetidine-2-carboxylate hydrochloride from Reference Example 1 (361.4 mg, 2.26 mmol, 1.0 eq) was dissolved in dry dichloromethane (10.0 mL) and treated with α-toluenesulfonyl chloride (458.1 mg, 2.40 mmol, 1.1 eq). After cooling to about 0° C. under argon atmosphere, diisopropylethylamine (420 μL, 2.41 mmol, 1.1 eq) was added and the reaction mixture was stirred at about room temperature overnight. The solvent was evaporated and the residue was subjected to flash chromatography (in dichloromethane) to give 431.2 mg (71 % yield) of the product as a colorless oil. $^1$H NMR (CDCl$_3$) δ 2.29–2.51 (m, 2H); 3.21–3.29 (m,1H); 3.81 (s, 3H); 4.02 (q,1H, J=8.6); 4.32 (d, 1H, J=9.4, 6.9); 4.46 (d, 1H, J=14.6); 4.86 (dd, 1H, J=9.4, 6.9); 7.34–7.43 (m, 3H); 7.46–7.54 (m, 2H).

Reference Example 8

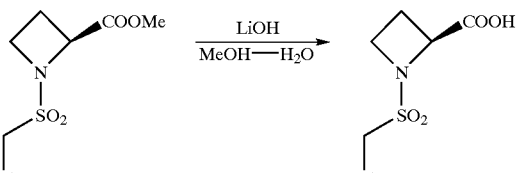

(2S)-1-(α-Toluenesulfonyl)azetidine-2-carboxylic
acid

To a solution of (2S)-Methyl-1-(α-toluenesulfonyl) azetidine-2-carboxylate from Reference Example 7 (378.4 mg; 1.40 mmol) in methanol (7.0 mL) was added 1N LiOH in water (2.6 mL) at about 0° C. The mixture was warmed to about room temperature and stirred under argon overnight. The pH was adjusted to about pH 1 by adding 1N HCl and then the mixture was diluted with water and extracted into ethyl acetate. The organic layer was dried over magnesium sulfate and then concentrated to give 335.7 mg (94% yield) of the product as a white solid. $^1$H NMR (CDCl$_3$) δ 2.37–2.57 (m, 2H); 3.21–3.31 (m, 1H); 4.01 (q, 1H, J=8.6); 4.33 (d, 1H, J=13.7); 4.44 (d, 1H, J=13.7); 4.98 (dd, 1H, J=9.4, 8.6); 7.34–7.53 (series of m, 5H).

Compound 8

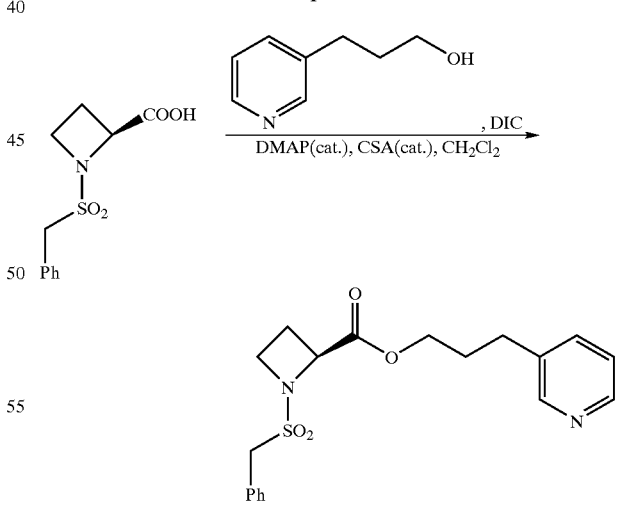

(2S)-[3-(3-Pyridyl)-1-propyl]-1-(α-toluenesulfonyl)
azetidine-2-carboxylate

A mixture of 2S-1-(α-toluenesulfonyl)-azetidine-2-carboxylic acid from Reference Example 8 (281.9 mg, 1.10 mmol, 1.0 eq), 3-(3-pyridyl)1-propanol (140 μL, 1.08 mmol, 1.0 eq), diisopropylcarbodiimide (260 μL, 1.66 mmol, 1.5 eq), camphorsulfonic acid (87 mg, 0.37 mmol, 0.34 eq) and dimethylaminopyridine (46 mg, 0.38 mmol, 0.34 eq) in dry dichloromethane (7 mL) was stirred at about room temperature for about 15 hours under argon. The solid was filtered off and washed with dichloromethane. The organic filtrate was concentrated and the residue was subjected to flash chromatography (in ether) to give 25.8 mg (6% yield) of the product as a colorless oil. $^1$H NMR (CDCl$_3$) δ 1.96–2.11 (m, 2H); 2.24–2.52 (m, 2H); 2.71 (t, 2H, J=8.6); 3.21–3.32 (m, 1H); 4.02 (q, 1H, J=8.6); 4.23 (t, 2H, J=6.9); 4.32 (d, 1H, J=14.6); 4.44 (d, 1H, J=14.6); 4.94 (dd, 1H, J=9.4, 8.6); 7.19–7.31 (m, 1H); 7.34–7.58 (m, 6H); 8.48 (s, 2H).

Reference Example 9

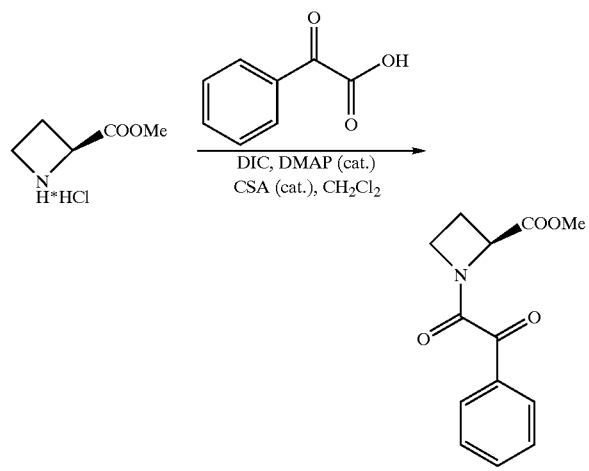

(2S)-Methyl-1-(1,2-dioxo-2-phenylethyl)azetidine-2-carboxylate

To a mixture of benzoylformic acid (600.5 mg, 4.00 mmol, 1.0 eq), diisopropylcarbodiimide (1.0 mL, 6.39 mmol, 1.6 eq), camphorsulfonic acid (171.7 mg, 0.74 mmol, 0.2 eq) and dimethylaminopyridine (87.5 mg, 0.72 mmol, 0.2 eq) in dry dichloromethane (30 mL) was added (2S) methyl azetidine-2-carboxylate (701.7 mg, 4.63 mmol, 1.2 eq) in dry dichloromethane (12 mL) at about room temperature. The mixture was stirred at about room temperature for about 24 hours under argon. The solid was filtered off and washed with ether. The organic filtrate was concentrated and the residue subjected to flash chromatography (2:1 ether:pentane) to give 532.1 mg (54% yield) of the product. $^1$H NMR (CDCl$_3$) δ 2.29–2.48 (m, 1H); 2.67–2.90 (m, 1H); 3.58 and 3.86 (s, 3H); 4.12–4.46 (series of m, 2H); 4.97 and 5.30 (dd, 1H, J=10.3, 6.0, J=10.3, 6.0); 7.47–7.69 (series of m, 3H); 8.09–8.23 (m, 2H).

Reference Example 10

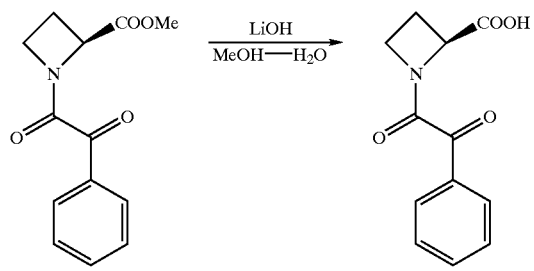

(2S)-1-(1,2-dioxo-2-phenylethyl)azetidine-2-carboxylic acid

To a solution of (2S)-methyl-1-(1,2-dioxo-2-phenylethyl) azetidine-2-carboxylate from Reference Example 9 (522.5 mg; 2.11 mmol) in a 1:1 mixture of ether:methanol (20.0 mL) was added 1N LiOH in water (3.9 mL) at about 0° C. The mixture was stirred under argon at about 0° C. for about 30 minutes and then at about room temperature overnight. The pH was adjusted to about pH 1 by adding 1N HCl and then the mixture was diluted with water and extracted with dichloromethane. The organic layers were then washed with brine, dried over sodium sulfate and concentrated to give 415.2 mg (67% yield) of the product as a yellow solid. $^1$H NMR (CDCl$_3$) δ 2.33–2.91 (series of m, 2H); 4.08–4.51 (series of m, 2H); 5.09 and 5.31 (dd, 1H, J=10.3, 6.9, J=10.3, 6.9); 7.40–7.73 (m, 3H); 8.04–8.19 (m, 2H); 8.25–8.80 (br, 1H).

Compound 9

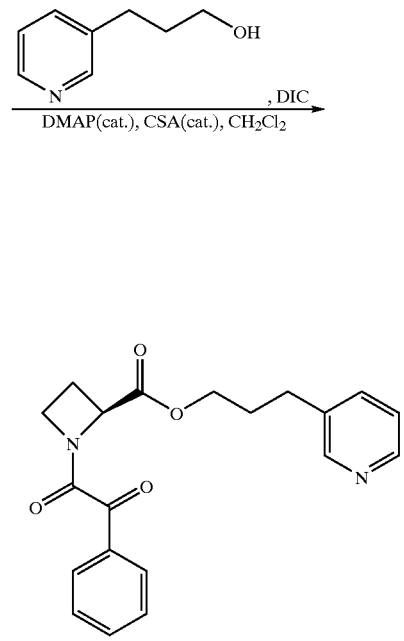

(2S)-[3-(3-Pyridyl1propyl]-1-(1,2-dioxo-2-phenylethyl)azetidine-2-carboxylate (2S)-1-(1,2-Dioxo-2-phenylethyl)azetidine-2-carboxylic acid from Reference Example 10 (402.2 mg, 1.72 mmol, 1.0 eq) was dissolved in dry dichloromethane (10 mL), to which was added 3-(3-pyridyl)-1-propanol (220 μl, 1.70 mmol, 1.0 eq), diisopropylcarbodiimide (430 μl, 2.75 mmol, 1.6 eq), camphorsulfonic acid (132.5 mg, 0.57 mmol, 0.33 eq) and dimethylaminopyridine (74.9 mg, 0.35 mmol, 0.35 eq) in that order. The mixture was stirred at about room temperature for about 15 hours under argon. The solid was filtered off and washed with dichloromethane. The organic filtrate was concentrated and the residue was subjected to flash chromatography (1:20 methanol:chloroform) to give 409.3 mg (67% yield) of the product as a colorless oil. $^1$H NMR (CDCl$_3$) δ 1.69–2.87 (series of m, 6H); 3.96–4.42 (m, 4H); 4.93 and 5.28 (dd, 1H, J=9.4, 6.9, J=9.4, 6.9); 7.13–7.68 (m, 5H); 8.07–8.18 (s, 2H); 8.32–8.52 (m, 2H).

Compound 10

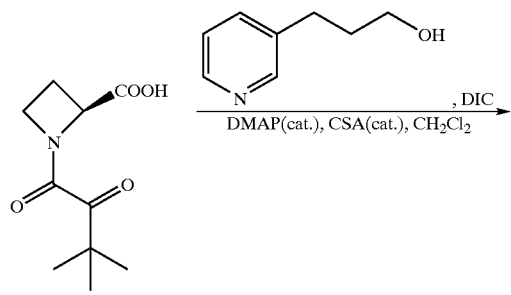

10

(2S)-[3-(3-Pyridyl)-1-propyl]-1-(1,2-dioxo-3,3-dimethylbutyl)azetidine-2-carboxylate The title compound was prepared as described for Compound 9 except that (2S)-1-(1,2-dioxo-3,3-dimethylbutyl)azetidine-2-carboxylic acid (from the corresponding methyl ester as described for Reference Example 10 above) was used in place of (2S)-1-(1,2-dioxo-2-phenylethyl)azetidine-2-carboxylic acid (6% yield). $^1$H NMR (CDCl$_3$) δ 1.18–1.37 (m, 9H); 1.94–2.79 (series of m, 6H); 4.00–4.43 (m, 4H); 4.83 and 5.23 (dd, 1H, J=9.4, 6.9, J=9.4, 6.9); 7.22–7.26 (m,1H); 7.53 (d,1H, J=7.7); 8.46 (s, 2H).

Compound 11

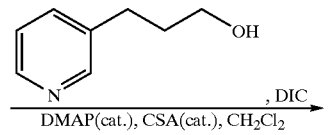

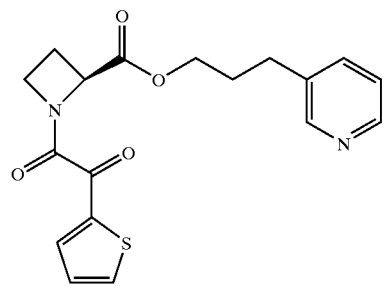

11

(2S)-[3-(3-Pyridyl)-1-propyl]-1-[1,2-dioxo-2-(thien-2-yl)ethyl]azetidine-2-carboxylate The title compound was prepared as described for Compound 9 except that (2S)-1-[1,2-dioxo-2-(thien-2-yl)ethyl]azetidine-2-carboxylic acid (from the corresponding methyl ester as described for Reference Example 10 above) was used in place of (2S)-1-(1,2-dioxo-2-phenylethyl)azetidine-2-carboxylic acid (6% yield). $^1$H NMR (CDCl$_3$) δ 1.85–2.90 (series of m, 6H); 4.08–4.72 (series of m, 4H); 4.92 and 5.39 (dd, 1H, J=9.4, 6.9, J=9.4, 6.9); 7.12–7.26 (m, 2H); 7.42–7.57 (m, 1H); 7.73–7.82 (m, 1H); 8.24 (d, 1H, J=4.3); 8.37–8.52 (m, 2H).

Compound 12

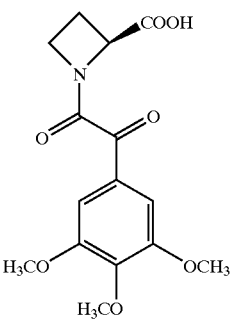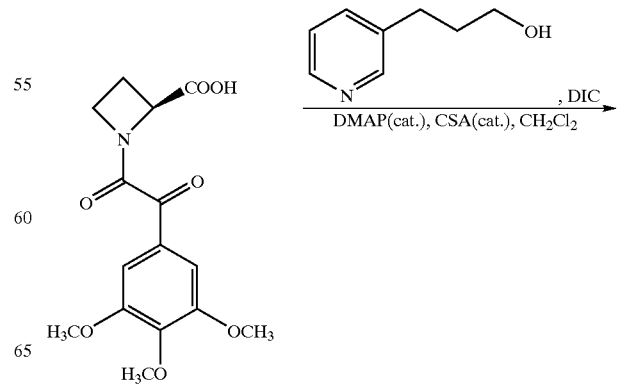

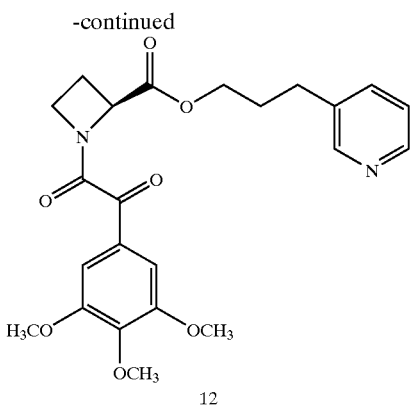

12

(2S)-[3-(3-Pyridyl)-1-propyl]-1-(1,2-dioxo-2-(3,4,5-trimethoxyphenyl)ethyl)azetidine-2-carboxylate The title compound was prepared as described for Compound 9 except that (2S)-1-[1,2-dioxo-2-(3,4,5-trimethoxyphenyl)ethyl]azetidine-2-carboxylic acid (from the corresponding methyl ester as described for Reference Example 10 above) was used in place of (2S)-1-(1,2-dioxo-2-phenylethyl)azetidine-2-carboxylic acid (46% yield). $^1$H NMR (CDCl$_3$) δ 1.71–2.88 (series of m, 6H); 3.84–3.98 (series of s, 9H); 4.07–4.43 (m, 4H); 4.95 and 5.32 (dd, 1H, J=9.4, 6.9, J=9.4, 6.9); 7.17–7.26 (m, 1H); 7.39–7.59 (m, 3H); 8.39–8.49 (m, 2H).

Reference Example 11

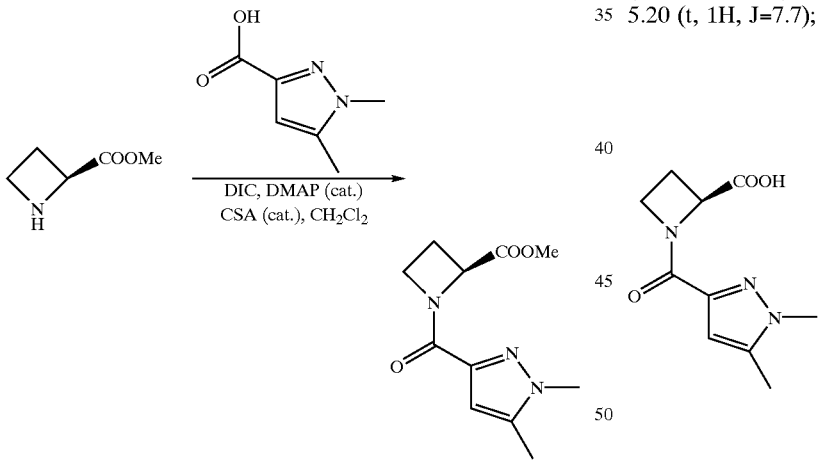

(2S)-Methyl-1-[(1,5-dimethylpyrazol-3-yl)carbonyl]azetidine-2-carboxylate

To a mixture of the 1,5-dimethylpyrazole-3-carboxylic acid (433.1 mg, 3.09 mmol, 1.0 eq), diisopropylcarbodiimide (0.74 mL, 4.73 mmol, 1.5 eq), camphorsulfonic acid (300.6 mg, 1.29 mmol, 0.4 eq) and dimethylaminopyridine (129.7 mg, 1.06 mmol, 0.3 eq) in dry dichloromethane (30 mL) was added (2S)-methyl azetidine-2-carboxylate (474.4 mg, 3.13 mmol, 1.0 eq) in dry dichloromethane (12 mL) at about room temperature. The mixture was stirred at about room temperature for about 24 hours under argon. The solid was filtered off and washed with ether. The organic filtrate was concentrated and the residue subjected to flash chromatography (1–10% methanol in dichloromethane) to give 429.9 mg (58% yield) of the product. $^1$H NMR (CDCl$_3$) δ 2.22–2.77 (series of s and m, 5H); 3.64–3.84 (series of s, 6H); 4.08–4.73 (series of m, 2H); 4.89 and 5.29 (dd, 1H, J=9.4, 6.0); 6.53 (s, 1H).

Reference Example 12

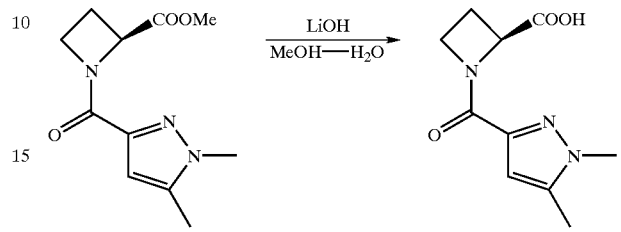

(2S)-1-[(1,5-dimethylpyrazol-3-yl)carbonyl]azetidine-2-carboxylic acid

To a solution of (2S)-methyl-1-[(1,5-dimethylpyrazol-3-yl)carbonyl]azetidine-2-carboxylate (398.4 mg, 1.68 mmol) in methanol (12 mL) was added 1N LiOH in water (3.1 mL) at about 0° C. The mixture was stirred under argon at about 0° C. for about 30 minutes and then at about room temperature overnight. The pH was adjusted to about pH 1 by adding 1 N HCl and then the mixture was diluted with water and extracted with dichloromethane. The organic layers were washed with brine, dried over sodium sulfate and then concentrated to give 315.2 mg (84% yield) of the product as a white solid. $^1$H NMR (CDCl$_3$) δ 2.32 (s, 3H); 2.49–3.89 (series of m, 2H); 3.84 (s, 3H); 4.40–4.71 (series of m, 2H); 5.20 (t, 1H, J=7.7); 6.57 (s, 1H).

Compound 13

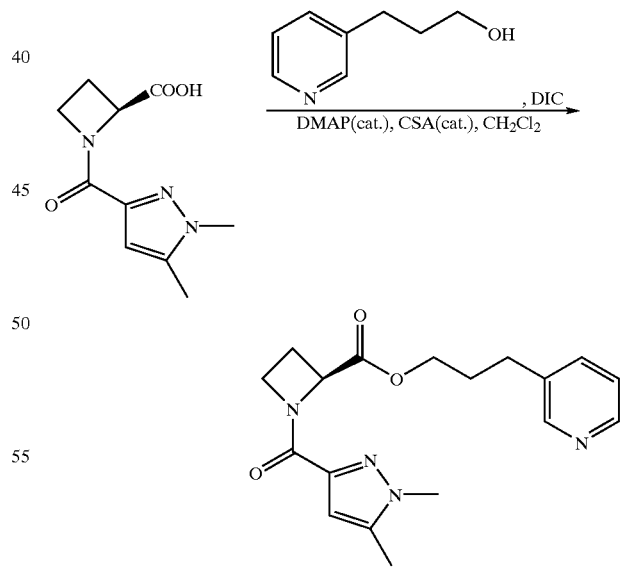

13

(2S)-[3-(3-Pyridyl)-1-propyl]-1-[(1,5-dimethylpyrazol-3-yl)carbonyl]azetidine-2-carboxylate (2S)-1-(1,5-dimethylpyrazol-3-yl)carbonyl]azetidine-2-carboxylic acid (129.6 mg, 0.58 mmol, 1.0 eq) was dissolved in dry dichloromethane (10 mL), to which was added 3-(3-pyridyl)-1-propanol (80 µL, 0.62 mmol, 1.07 eq), diisopropylcarbodiimide (140 µL, 0.89 mmol, 1.53 eq), camphorsulfonic acid (46.3 mg, 0.2 mmol, 0.34 eq) and dimethylaminopyridine (29.2 mg, 0.24 mmol, 0.48 eq) in that order. The mixture was stirred at about room temperature for about 15 hours under argon. The solid was filtered off and washed with dichloromethane. The organic filtrate was concentrated and the residue was subjected to flash chromatography (1–10% methanol in chloroform) to give 191.6 mg (96% yield) of the product as a colorless oil. $^1$H NMR (CDCl$_3$) δ 1.78–2.82 (series of m and s, 9H); 3.61–3.82 (series of s, 3H); 3.82–4.74 (series of m, 4H); 4.89 and 5.32 (dd, 1H, J=10.3, 6.0, J=10.3, 6.0); 6.50–6.57 (series of s, 1H); 7.18–7.24 (m, 1H); 7.40 and 7.54 (d, 1H, J=7.7, J=7.7); 8.28–8.49 (series of nd, 2H).

Reference Example 13

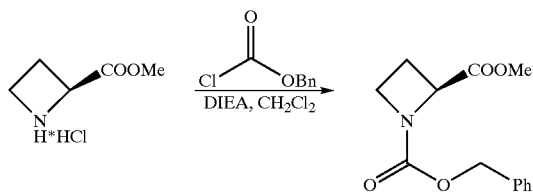

(2S)-Methyl-1-(benzyloxycarbonyl)azetidine-2-carboxylate (2S)-Methyl azetidine-2-carboxylate (2.83 g, 18.7 mmol, 1.0 eq) was dissolved in dry dichloromethane (100 mL) and cooled to about 0° C. under an argon atmosphere. After the addition of benzyl chloroformate (3.00 mL, 20.0 mmol, 1.1 eq), diisopropyl ethylamine (8.00 mL, 45.9 mmol, 2.5 eq) was added to the mixture dropwise. The reaction mixture was stirred at about 0° C. for about 30 minutes and then at about room temperature overnight. The solvent was evaporated and then the residue was dissolved in ether, washed with 1N HCl, water and brine, dried over magnesium sulfate and concentrated. Flash chromatography (in ether) gave 3.75 g (80% yield) of the product as a colorless oil. $^1$H NMR (CDCl$_3$) δ 2.19–2.32 (m, 1H); 2.52–2.66 (m, 1H); 3.74 (s, 3H); 3.94–4.03 (m, 1H); 4.08–4.18 (m, 1H); 4.72 (dd, 1H, J=9.4, 6.9); 5.12 (q, 2H, J=12.9); 7.29–7.42 (m, 5H).

Reference Example 14

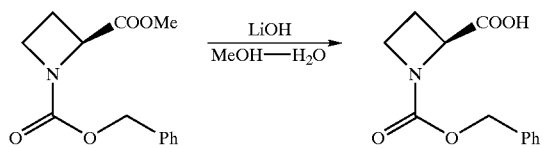

(2S)-1-(Benzyloxycarbonyl)azetidine-2-carboxylic acid

To a solution of (2S)-methyl-1-(benzyloxycarbonyl) azetidine-2-carboxylate (0.78 g, 3.12 mmol) in a 1:1 mixture of ether:methanol (25.0 mL) was added 1N LiOH in water (5.8 mL) at about 0° C. The mixture was stirred under argon at about 0° C. for about 30 minutes and then at about room temperature overnight. The pH was adjusted to about pH 1 by adding 1N HCl, then the mixture was diluted with water and extracted with dichloromethane. The organic layer was washed with brine, dried over sodium sulfate and concentrated to give 0.78 g (99% yield) of the product as a colorless oil. $^1$H NMR (CDCl$_3$) δ 2.45–2.63 (br, 2H); 4.00 (t, 2H, J=7.7); 4.77–4.90 (br, 1H); 5.16 (s, 2H); 7.37 (s, 5H).

Reference Example 15

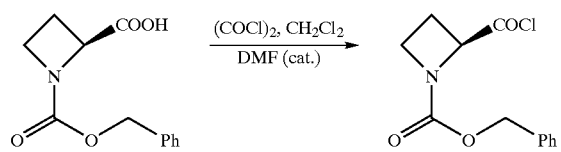

(2S)-1-(Benzyloxycarbonyl)azetidine-2-carboxylic acid chloride (2S)-1-(benzyloxycarbonyl)azetidine-2-carboxylic acid (729.3 mg, 3.10 mmol, 1.0 eq) was dissolved in dry dichloromethane (15 mL) and cooled to about –5° C. under argon. Oxalyl chloride (380 µL, 4.36 mmol, 1.4 eq) and a drop of DMF were added to the solution. The mixture was warmed to reflux temperature with stirring over about a 3 hour period. After cooling, the mixture was concentrated and used in Reference Example 16.

Reference Example 16

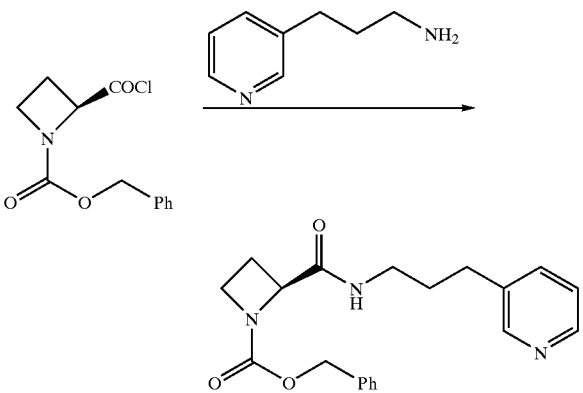

(2S)-N-[3-(3-Pyridyl)-1-propyl]-1-(benzyloxycarbonyl)azetidine-2-carboxamide

The product of Reference Example 15 was dissolved in dry dichloromethane (20 mL) and added to a solution of 3-(3-pyridyl)propylamine (694.7 mg, 4.73 mmol, 1.5 eq) in dichloromethane and cooled to about 0° C. under argon. The mixture was stirred at about room temperature overnight, concentrated in vacuo, treated with water and extracted with ethyl acetate. The organic solution was dried over magnesium sulfate, then concentrated and subjected to flash chromatography (1–10% methanol in dichloromethane) to give 295.7 mg (27% yield for two steps) of the product as a colorless oil. $^1$H NMR (CDCl$_3$) δ 1.70–1.95 (br, 3H); 2.48–2.70 (br, 4H); 3.20–3.44 (m, 2H); 3.88 (q, 1H, J=8.6); 4.02 (q, 1H, J=8.6); 4.73 (t, 1H, J=7.7); 5.16 (q, 2H, J=12.01); 7.18–7.54 (series of m, 7H); 8.39–8.50 (m, 2H).

Reference Example 17

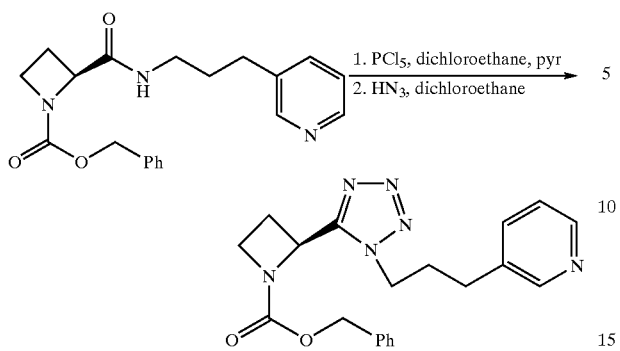

(2S)-1-(Benzyloxycarbonyl)2-(1-[3-(3-pyridyl)-1-propy]-1H-tetrazol-5-yl)-azetidine To a solution of (2S)-N-[3-(3-Pyridyl)-1-propyl]-1-(benzyloxycarbonyl)azetidine-2-carboxamide from Reference Example 16 (295.7 mg, 0.837 mmol, 1.0 eq) in dry 1,2-dichloroethane (8.5 mL) was added pyridine (100 μL, 1.24 mmol, 1.5 eq) under argon. Phosphorus pentachloride (263 mg, 1.26 mmol, 1.5 eq) was added in one portion and the mixture was stirred at about room temperature for about 4 hours. A dry $HN_3$ solution (prepared by mixing 6.5 g of $NaN_3$ in 25 mL of water with 8.3 mL conc. HCl, extracting with 25 mL 1,2-dichloroethane, drying over magnesium sulfate and filtering) was added and the reaction mixture was stirred at about room temperature overnight. The organic phase was washed with concentrated $NH_4OH$ solution (2×5 mL), dried and the solvents removed under vacuum. Flash chromatography (5–10% methanol in dichloromethane) gave 125.3 mg (40% yield) of the product as a colorless oil. $^1$H NMR (CDCl$_3$) δ 2.11–3.51 (series of m, 7H); 4.08–5.40 (series of m, 6H); 7.12–7.57 (m, 7H); 8.37–8.51 (m, 2H).

Reference Example 18

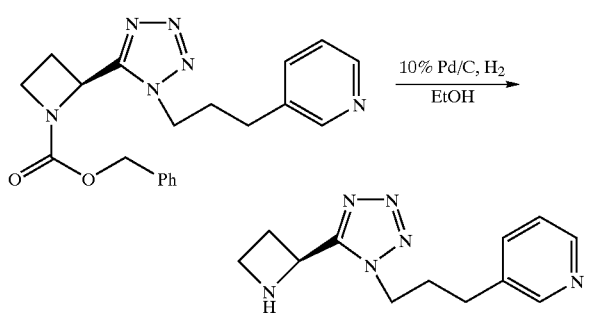

(2S)-2-(1-[3-(3-Pyridyl)-1-propyl]-1H-tetrazol-5-yl)azetidine (2S)-1-(Benzyloxycarbonyl)-2-(1-[3-(3-pyridyl)-1-propyl]-1H-tetrazol-5-yl)azetidine from Reference Example 17 (125.3 mg, 0.331 mmol, 1.0 eq) was dissolved in ethanol (20 mL) and 10% Pd/C (49.9 mg, 0.047 mmol, 0.14 eq) was carefully added. The mixture was flushed with vacuum and nitrogen three times and stirred under a hydrogen atmosphere at about room temperature for about 26 hours. After removing the solid matter by filtration, the solvent was removed under vacuum to give 80.8 mg (quantitative yield) of the product as a colorless oil. $^1$H NMR (CDCl$_3$) δ 2.18–3.24 (series of m, 7H); 3.46–4.68 (series of m, 5H); 7.19–7.33 (m, 1H); 7.51–7.63 (m, 1H); 8.38–8.57 (m, 2H).

Reference Example 19

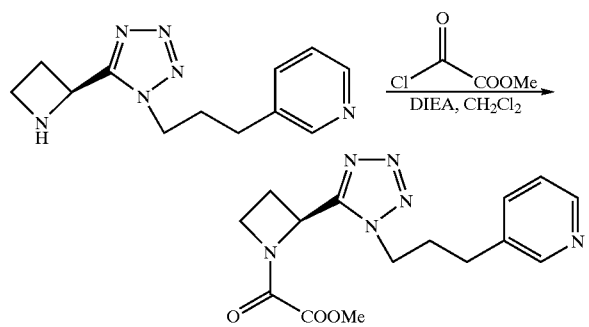

(2S)-1-(1,2-dioxo-2-methoxyethyl)-2-(1-[3-(3-pyridyl)-1-propyl]-1H-tetrazol-5-yl)azetidine (2S)-2-(1-[3-(3-Pyridyl)-1-propyl]-1H-tetrazol-5-yl)azetidine from Reference Example 18 (80.8 mg, 0.331 mmol, 1.0 eq) was dissolved in dry dichloromethane (1.0 mL) and cooled to about 0° C. under an argon atmosphere. After adding methyl oxalyl chloride (40 μL, 0.43 mmol, 1.3 eq), diisopropylethylamine (500 μL, 3.5 mmol, 10.0 eq) was added to the mixture. The reaction mixture was stirred at about 0° C. for about 30 minutes and at about room temperature for about 2 hours. The solvent was evaporated and the residue subjected to flash chromatography (0–10% methanol in dichloromethane) to give 95.8 mg (88% yield) of the product as a yellow oil. $^1$H NMR (CDCl$_3$) δ 1.77–3.35 (series of m, 8H); 3.68 and 3.87 (s, 3H); 4.22–4.89 (series of m, 2H); 5.37–6.02 (series of m, 1H); 7.22–7.31 (m, 1H); 7.58 (d, 1H, J=7.7); 8.44–8.53 (m, 2H).

Compound 14

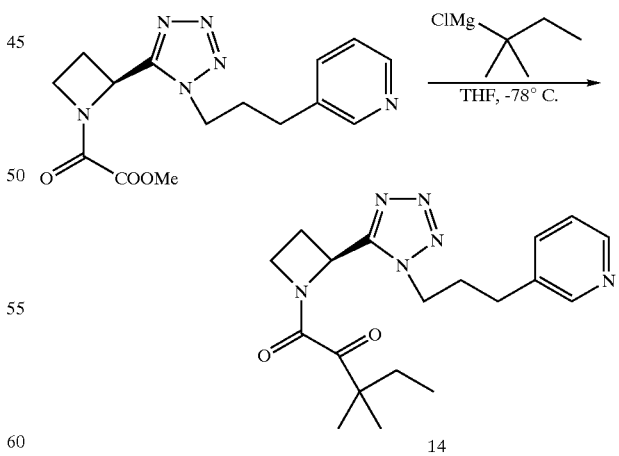

(2S)-1-(1,2-Dioxo-3,3-dimethylpentyl)2-(1-[3-(3-pyridyl)-1-propyl]-1H-tetrazol-5-yl)azetidine (2S)-1-(1,2-Dioxo-2-methoxyethyl)-2-(1-[3-(3-pyridyl)-1-propyl]-1H-tetrazol-5-yl)azetidine from Reference Example 19 (95.8 mg, 0.290 mmol, 1.0 eq) was dissolved in dry tetrahydrofuran (THF) (1.0 mL) and cooled to about −78° C. under an argon atmosphere. To this solution, 1,1-dimethylpropylmagnesium chloride in THF (380 μL of 1M, 0.380 mmol, 1.3 eq) was introduced via syringe. After stirring the resulting homogeneous mixture at about −78° C. for about 3 hours, the mixture was poured into saturated ammonium chloride and extracted into ethyl acetate. The organic phase was washed with water, dried over sodium sulfate and concentrated. Flash chromatography of the residue (0–10% methanol in dichloromethane) afforded 8.7 mg (8% yield) of the product as a colorless semisolid along with 30.3 mg recovered starting material (32% yield). $^1$H NMR (CDCl$_3$) δ 0.78 (t, 3H, J=6.9); 0.97–1.18 (series of s, 6H); 1.54 and 3.17 (series of m, 8H); 3.82–4.66 (series of m, 4H); 5.33–5.90 (series of dd, 1H); 7.21–7.31 (m, 1H); 7.57 (d, 1H, J=7.7); 8.49 (s, 2H).

Reference Example 20

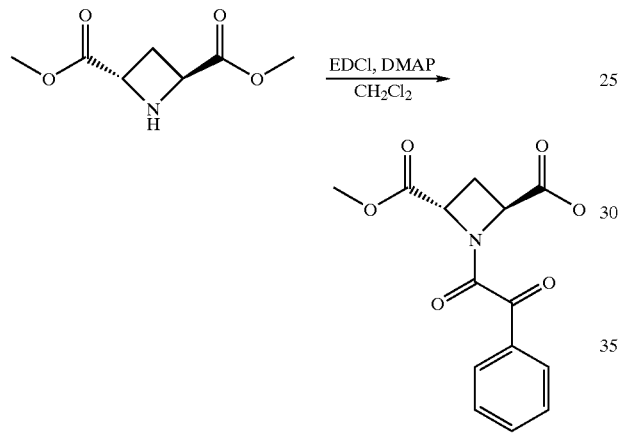

(2S,4S)-Dimethyl-1-(1,2-dioxo-2-phenylethyl)azetidine-2,4-dicarboxylate

A mixture of (2S,4S)-dimethyl azetidine-2,4-dicarboxylate (0.50 g, 2.9 mmol, 1.0 eq), benzoylformic acid (0.53 g, 3.2 mmol, 1.1 eq), EDCl (0.83 g, 4.3 mmol, 1.5 eq) and DMAP (0.71 g, 5.8 mmol, 2.0 eq) in 15.0 mL dichloromethane was stirred under nitrogen at about room temperature for about 24 hours. The solvent was evaporated and the residue was subjected to flash chromatography (1:1 hexane:ethyl acetate) to give 0.13 g (15% yield) of the product as a colorless oil. $^1$H NMR (CDCl$_3$) δ 2.62–2.80 (m, 2H); 3.66 (s, 3H); 3.84 (s, 3H); 4.97 (dd, 1H, J=8.6, 5.9); 5.35 (dd, 1H, J=8.6, 5.9); 7.49 (t, 2H); 7.63 (t, 1H); 8.16 (d, 2H, J=11.1).

Reference Example 21

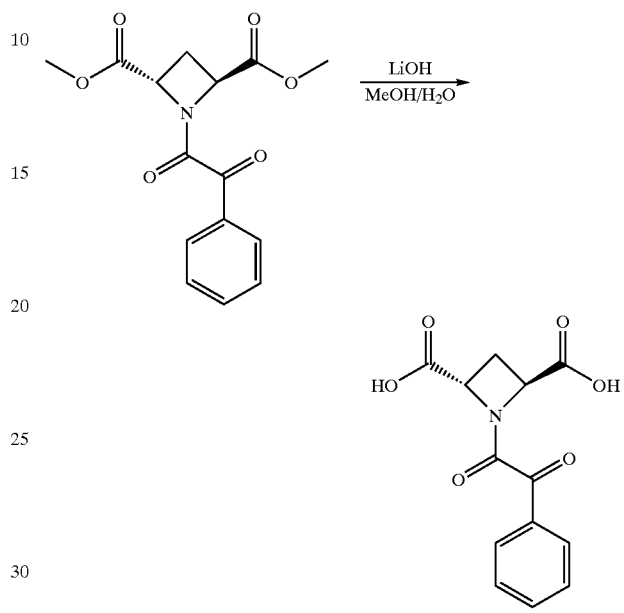

(2S,4S)-1-(1,2-dioxo-2-phenylethyl)azetidine-2,4-dicarboxylic acid

To the solution of (2S,4S)-dimethyl-1-(2-phenyl-1,2-dioxoethyl)azetidine-2,4-dicarboxylate from Reference Example 20 (0.12 g, 0.39 mmol) in methanol (3.0 mL) was added 1N LiOH in water (1.6 ml) at about 0° C. The mixture was stirred under nitrogen at about 0° C. for about 30 minutes and then at about room temperature overnight. The pH was adjusted to about pH 1 by using 1N HCl and the mixture was extracted with ethyl acetate. The organic layers were dried over magnesium sulfate and then concentrated to give 0.11 g (97% yield) of the product as a white solid. $^1$H NMR (DMSO) δ 2.62–2.74 (m, 2H); 4.73–4.81 (m, 1H); 5.05–5.14 (m, 1H); 7.57 (t, 2H); 7.72 (t, 1H); 8.00 (d, 2H).

Compound 15

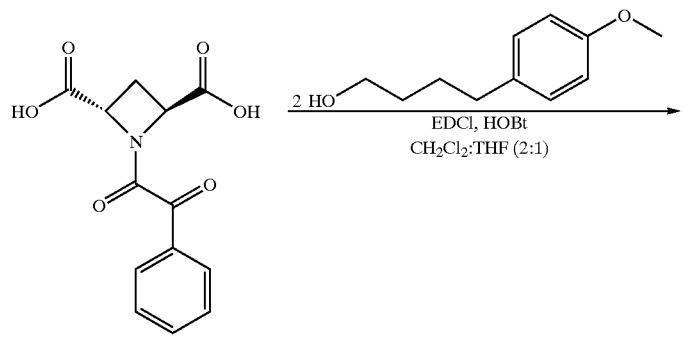

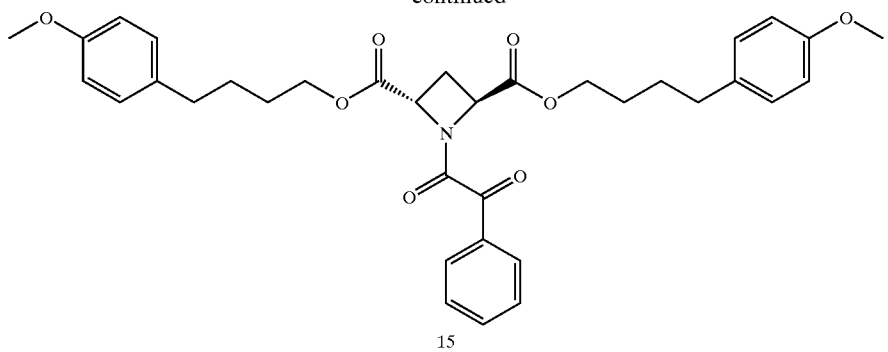

(2S,4S)-Bis-[4-(4-methoxyphenyl)-1-butyl)-1-(1,2-dioxo-2-phenylethyl)azetidine-2,4-dicarboxylate A mixture of (2S,4S)-1-(2-phenyl-1,2-dioxoethyl) azetidine-2,4-dicarboxylic acid (42 mg, 0.15 mmol, 1.0 eq), 4-methoxyphenyl-1-butanol (0.1 mL, 0.6 mmol, 4.0 eq), EDCl (73 mg, 0.38 mmol, 2.5 eq) and HOBt (51 mg, 0.38 mmol, 2.5 eq) in dichloromethane (2.0 mL) was stirred at about room temperature for about 24 hours. After concentrating, the residue was subjected to flash chromatography (1:1 hexane:ethyl acetate) to give 45 mg (49% yield) of the product as a colorless oil. $^1$H NMR (CDCl$_3$) δ 1.48–1.56 (m, 4H); 1.63–1.76 (m, 4H); 2.44–2.52 (m, 2H); 2.53–2.76 (m, 4H); 3.78 (s, 3H); 3.79 (s, 3H); 4.02–4.11 (m, 2H); 4.20–4.28 (m, 2H); 4.93 (dd,1H, J=9.4, 6.9); 5.32 (dd,1H, J=9.0, 6.9); 6.81 (dd, 4H, J=7.7, 3.4); 7.07 (dd, 4H, J=12.9, 9.8); 7.45(t, 2H); 7.61 (t, 1H); 8.13 (d, 2H, J=10.3).

Reference Example 22

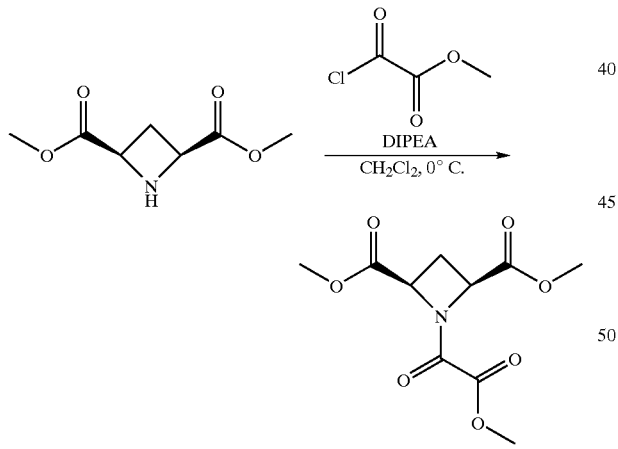

(2S,4R)-Dimethyl-1-(1,2-dioxo-2-methoxyethyl)azetidine-2,4-dicarboxylate (2S,4R)-Dimethyl azetidine-2,4-dicarboxylate (1.69 g, 9.76 mmol, 1.0 eq) was dissolved in dry dichloromethane (25.0 mL) and cooled to about 0° C. under argon atmosphere. After adding methyl oxalyl chloride (0.9 mL, 9.78 mmol, 1.0 eq), diisopropylethylamine (1.75 mL, 10.1 mmol, 1.0 eq) was added to the mixture. Then the reaction mixture was stirred at about 0° C. for about 30 minutes and at about room temperature for about 18 hours. The solvent was evaporated and the residue was subjected to flash chromatography (1:1 ether:dichloromethane) to give 1.94 g (77% yield) of the product as a yellow oil. $^1$H NMR (CDCl$_3$) δ 2.41–2.49 (m, 1H); 2.99–3.10 (m, 1H); 3.82 (s, 3H); 3.83 (s, 3H); 3.87 (s, 3H); 4.83 (dd,1H, J=9.4, 6.9); 5.29 (dd, 1H, J=9.4, 6.9).

Reference Example 23

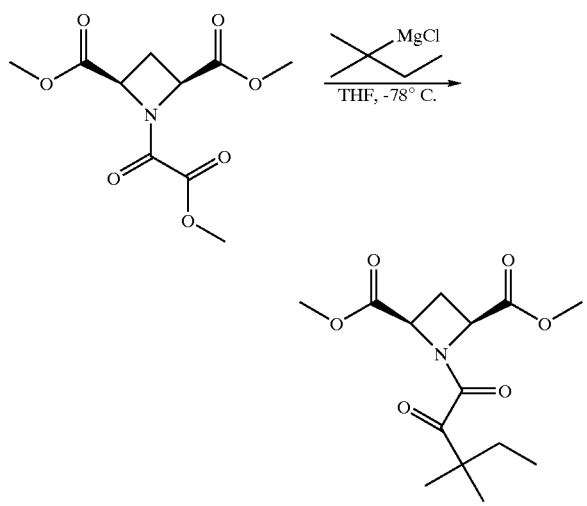

(2S,4R)-Dimethyl-1-(1,2-dioxo-3,3-dimethylpentyl)azetidine-2,4-dicarboxylate (2S,4R)-Dimethyl-1-(1,2-dioxo-2-methoxyethyl) azetidine-2,4-dicarboxylate from Reference Example 22 (1.93 g, 7.45 mmol, 1.0 eq) was dissolved in dry THF (25.0 mL) and cooled to about −78° C. 1,1-Dimethylpropylmagnesium chloride in THF (9.6 mL of 1M, 9.6 mmol, 1.3eq) was added under argon atmosphere. After stirring the resulting homogeneous mixture at about −78° C. for about 3 hours, the mixture was poured into saturated ammonium chloride (75 mL) and extracted into ethyl acetate at about 0° C. The organic phase was dried over sodium sulfate and concentrated. The residue was subjected to flash chromatography (1:1 ether:pentane) to give 0.93 g (42% yield) of the product as a colorless oil. $^1$H NMR (CDCl$_3$) δ 0.85 (t, 3H, J=8.6); 1.22 (s, 3H); 1.35 (s, 3H); 1.72 (dq, 1H, J=14.6, 8.6); 1.93 (dq, 1H, J=14.6, 8.6); 2.41 (dt, 1H, J=12.9, 5.6); 2.99 (dt, 1H, J=12.9, 9.4); 3.77 (s, 3H); 3.79 (s, 3H); 4.78 (dd, 1H, J=9.4, 5.6); 5.23 (dd, 1H, J=9.4, 5.6).

Reference Example 24

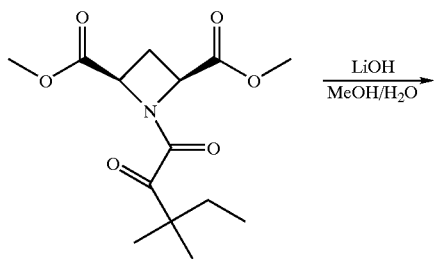

(2S,4R)-1-(1,2-dioxo-3,3-dimethylpentyl)azetidine-2,4-dicarboxylic acid

To a solution of (2S,4R)-dimethyl-1-(1,2-dioxo-3,3-dimethylpentyl)azetidine-2,4-dicarboxylate from Reference Example 23 (0.41 g, 1.37 mmol) in methanol (9.0 mL) was added 1N LiOH in water (3.0 mL) at about 0° C. The mixture was stirred under nitrogen at about 0° C. for about 30 minutes and then at about room temperature overnight. The pH was adjusted to about pH 1 with 1N HCl (4 mL) and the mixture was extracted with chloroform. The organic layers were dried over sodium sulfate and then concentrated to give 0.25 g (68%) of the product as a yellow solid. $^1$H NMR (DMSO) δ 0.97 (t, 3H); 1.11 (s, 3H); 1.25 (s, 3H); 1.52–1.68 (m, 1H); 1.73–1.89 (m, 1H); 2.14–2.28 (m, 1H); 2.93 (dd, 1H); 4.60 (dd, 1H); 5.06 (dd, 1H); 12.75–13.27 (broad).

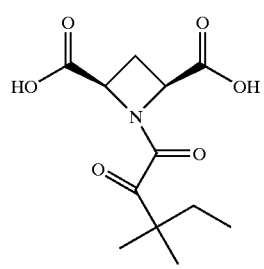

Compound 16

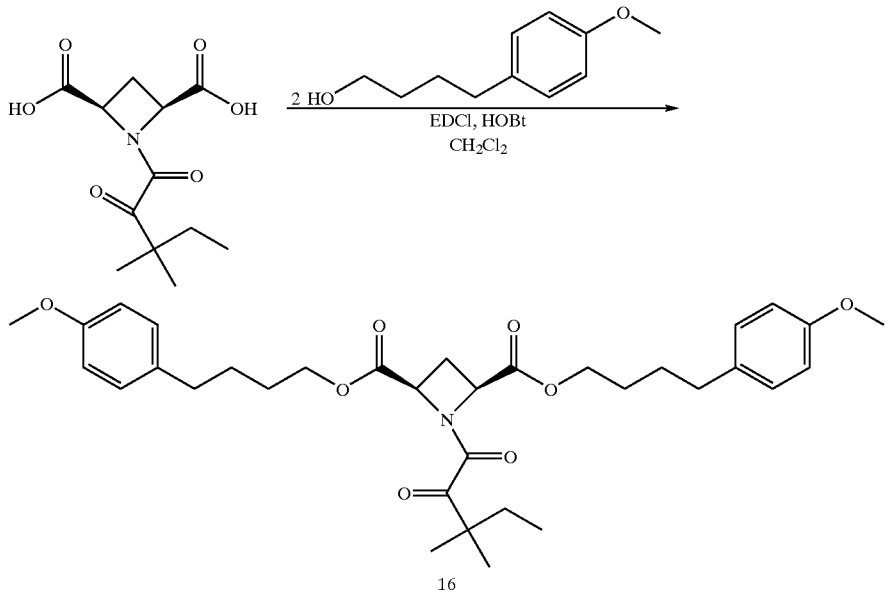

(2S,4R)-Bis-[4-(4-methoxyphenyl)-1-butyl]-1-(1,2-dioxo-3,3-dimethylpentyl)azetidine-2,4-dicarboxylate A mixture of (2S,4R)-1-(1,2-dioxo-3,3-dimethylpentyl)azetidine-2,4-dicarboxylate acid from Reference Example 24 (23 mg, 0.085 mmol, 1.0 eq), 4-methoxyphenyl-1-butanol (59 μL, 0.34 mmol, 4.0 eq), EDCl (41 mg, 0.21 mmol, 2.5 eq) and HOBt (29 mg, 0.21 mmol, 2.5 eq) in dichloromate (1.0 mL) was stirred at about room temperature for about 36 hours. After concentrating, the residue was subjected to flash chromatography (3:1 hexane:ethyl acetate) to give 46 mg (90% yield) of the product as a colorless oil. $^1$H NMR (CDCl$_3$) δ 0.82 (t, 3H, J=7.5); 1.18 (s, 3H); 1.20–1.30 (m, 4H); 1.31 (s, 3H); 1.59–1.76 (m, 5H); 1.84–1.98 (m, 1H); 2.28–2.38 (m, 1H); 2.50–2.62 (m, 4H); 2.89–3.02 (m, 1H); 3.78 (s, 6H); 4.05–4.22 (m, 4H); 4.73 (dd, 1H, J=9.4 6.9); 5.19 (dd, 1H, J=9.4, 6.9); 6.82 (dd, 4H, J=8.6, 3.4); 7.08 (dd, 4H, J=8.6, 4.2).

Compound 17

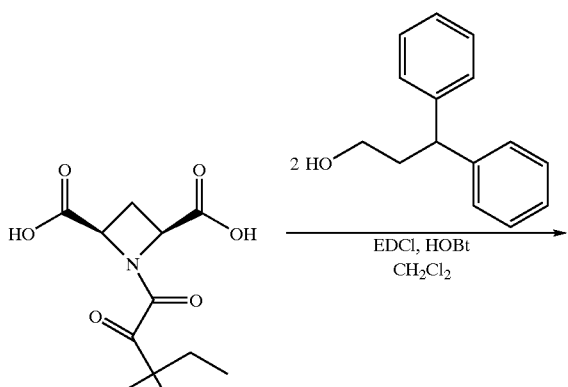

(2S,4R)-Bis-(3,3-diphenyl-1-propyl)-1-(1,2-dioxo-3,3-dimethylpentyl)azetidine-2,4-dicarboxylate The title compound was prepared as described for Compound 16 except that 3,3-diphenyl-1-propanol was used in place of 4-(4-methoxyphenyl)-1-butanol (62% yield). ¹H NMR (CDCl₃) δ0.78 (t, 3H, J=7.5); 1.26 (s, 3H); 1.28 (s, 3H); 1.63–1.77 (m, 1H); 1.83–1.98 (m, 1H); 2.22–2.32 (m, 1H); 2.33–2.43 (m, 4H); 2.86–2.98 (m, 1H); 3.88–4.19 (m, 6H); 4.72 (dd, 1H, J=9.4, 6.9); 5.18 (dd, 1H, J=9.4, 6.9); 7.12–7.31 (m, 20H).

Compound 18

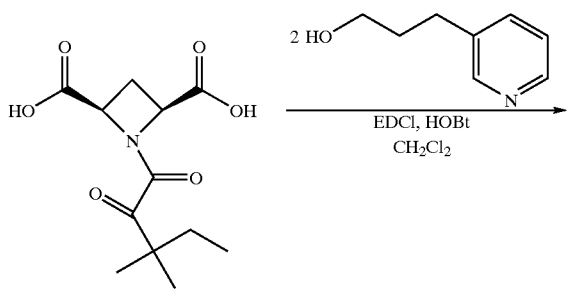

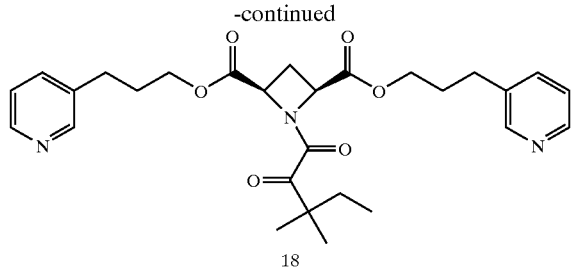

(2S,4R)-Bis-[3-(3-pyridyl)-1-propyl]-1-(1,2-dioxo-3,3-dimethylpentyl)azetidine-2,4-dicarboxylate The title compound was prepared as described for Compound 16 except that 3-(3-pyridyl)-1-propanol was used in place of 4-(4-methoxyphenyl)-1-butanol (71% yield). ¹H NMR (CDCl₃) δ0.82 (t, 3H, J=7.6); 1.20 (s, 3H); 1.32 (s, 3H); 1.66–1.80 (m, 1H); 1.84–2.07 (m, 4H); 2.32–2.42 (m, 1H); 2.66–2.78 (m, 4H); 2.93–3.07 (m, 1H); 3.69 (t, 1H, J=6.3); 4.09–4.12 (m, 4H); 4.78 (dd, 1H, J=9.4, 6.9); 5.24 (dd, 1H, J=9.9, 7.7); 7.19–7.27 (m, 2H); 7.49–7.59 (m, 2H); 8.41–8.51 (m, 4H).

Reference Example 25

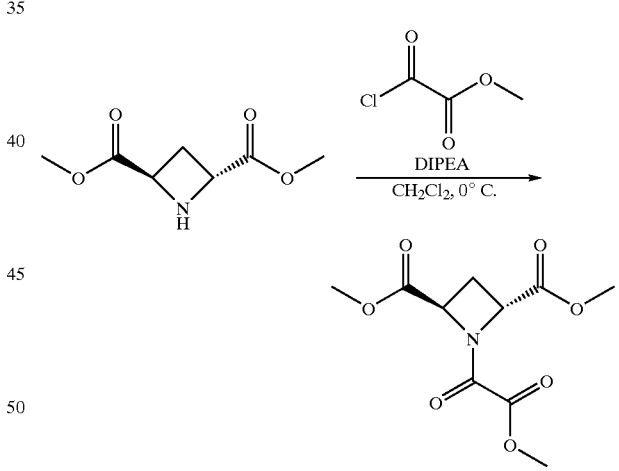

(2R,4R)-Dimethyl-1-(1,2-dioxo-2-methoxyethyl)azetidine-2,4-dicarboxylate

The title compound was prepared as described for Reference Example 22 except that (2R,4R)-dimethyl azetidine-2,4-dicarboxylate was used in place of (2S,4R)-dimethyl azetidine-2,4-dicarboxylate. MS: 260 (M+H, 22) and 282 (M+Na, 100).

Reference Example 26

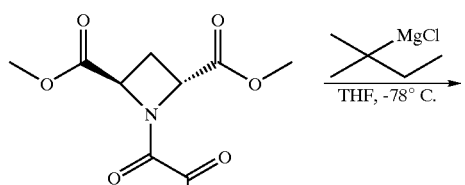

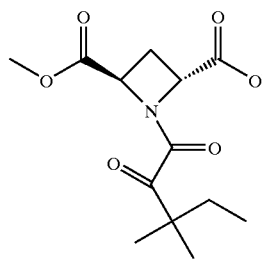

(2R,4R)-Dimethyl-1-(1,2-dioxo-3,3-dimethylpentyl)azetidine-2,4-dicarboxylate

The title compound was prepared as described for Reference Example 23 except that (2R,4R)-dimethyl-1-(1,2-dioxo-2-methoxyethyl)azetidine-2,4-dicarboxylate from Reference Example 25 was used in place of (2S,4R)-dimethyl-1-(1,2-dioxo-2-methoxyethyl)azetidine-2,4-dicarboxylate. MS: 300 (M+H, 7) and 322 (M+Na, 100).

Reference Example 27

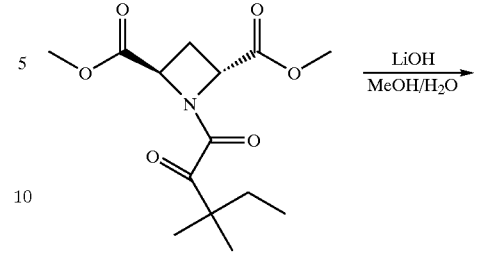

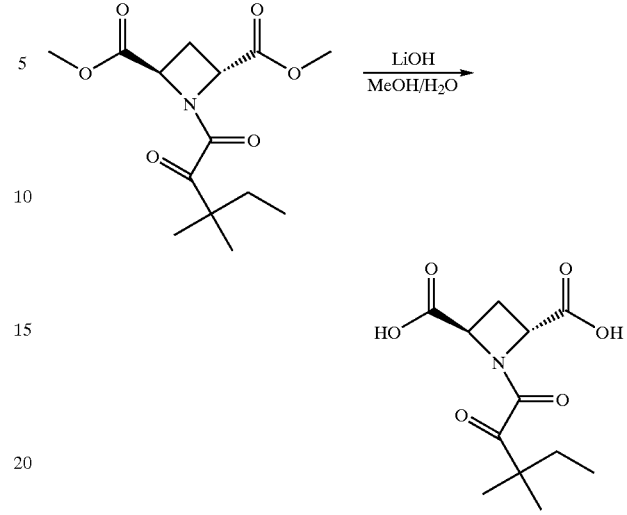

(2R,4R)-1-(1,2-dioxo-3,3-dimethylpentyl)azetidine-2,4-dicarboxylic acid

The title compound was prepared as described for Reference Example 24 except that (2R,4R)-dimethyl-1-(1,2-dioxo-3,3-dimethylpentyl)azetidine-2,4-dicarboxylate from Reference Example 26 was used in place of (2S,4R)-dimethyl-1-(1,2-dioxo-3,3-dimethylpentyl)azetidine-2,4-dicarboxylate. MS: 272 (M+H, 6) and 294 (M+Na, 100).

Compound 19

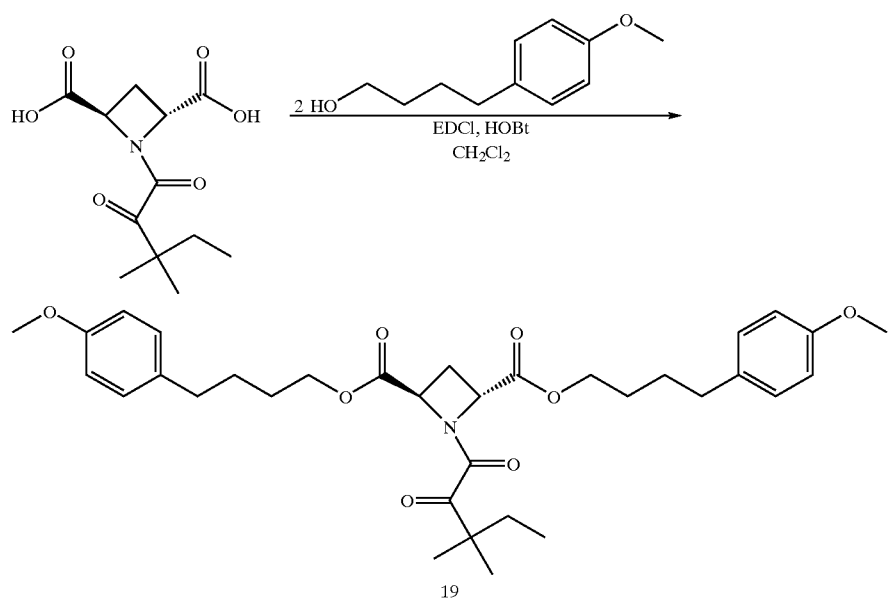

(2R,4R)-Bis-[4-(4-methoxyphenyl)-1-butyl]-1-(1,2-dioxo-3,3-dimethylpentyl)azetidine-2,4-dicarboxylate The title compound was prepared as described for Compound 16 except that (2R,4R)-1-(1,2-dioxo-3,3-dimethylpentyl)azetidine-2,4-dicarboxylate from Reference Example 27 was used in place of (2S,4R)-1-(1,2-dioxo-3,3-dimethylpentyl)azetidine-2,4-dicarboxylate (17% yield). ¹H NMR (CDCl₃) δ0.79 (t, 3H, J=7.6); 1.19–1.36 (overlapped, 10H); 1.61–1.80 (overlapped, 5H); 1.81–1.93 (m, 1H); 2.42–2.66 (overlapped, 6H); 3.78 (s, 6H); 4.08–4.26 (m, 4H); 4.80 (dd, 1H, J=9.0,6.9); 5.24 (dd, 1H, J=9.4,6.9); 6.83 (d, 4H, J=9.9); 7.10 (d, 4H, J=8.5).

Compound 20

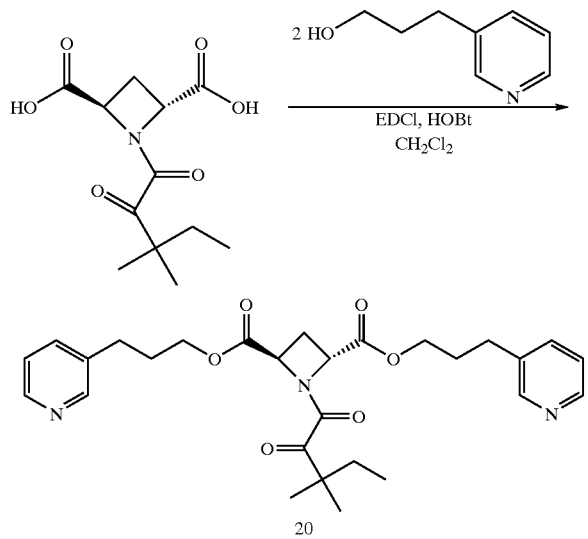

(2R,4R)-Bis-[3-(3-pyridyl)-1-propyl]-1-(1,2-dioxo-3,3-dimethylpentyl)azetidine-2,4-dicarboxylate The title compound was prepared as described for Compound 18 except that (2R,4R)-1-(1,2-dioxo-3,3-dimethylpentyl)azetidine-2,4-dicarboxylate from Reference Example 27 was used in place of (2S,4R)-1-(1,2-dioxo-3,3-dimethylpentyl)azetidine-2,4-dicarboxylate (40% yield). ¹H NMR (CDCl₃) δ0.82 (t, 3H, J=7.7); 1.21 (s, 3H); 1.29 (s, 3H); 1.71–1.96 (overlapped, 2H); 1.96–2.08 (m, 4H); 2.47–2.78 (overlapped, 6H); 4.09–4.32 (m, 4H); 4.86 (dd, 1H, J=9.4, 6.9); 5.28 (dd, 1H, J=9.4, 6.9); 7.22–7.31 (m, 2H); 7.36 (d, 2H, J=9.4); 8.27 (broad, 4H).

Reference Example 28

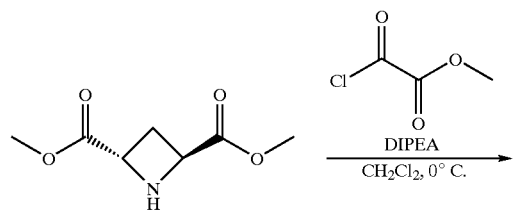

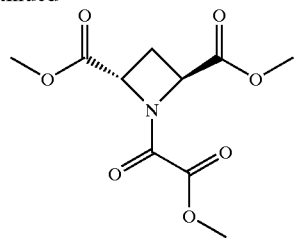

(2S,4S)-Dimethyl-1-(1,2-dioxo-2-methoxyethyl)azetidine-2,4-dicarboxylate

The title compound was prepared as described for Reference Example 22 except that (2S,4S)-dimethyl azetidine-2,4-dicarboxylate was used in place of (2S,4R)-dimethyl azetidine-2,4-dicarboxylate. MS: 260 (M+H, 16) and 282 (M+Na, 100).

Reference Example 29

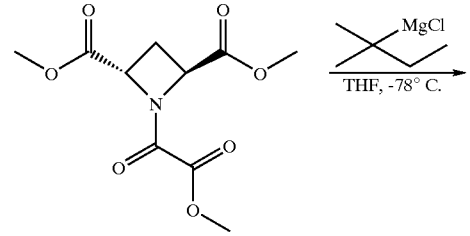

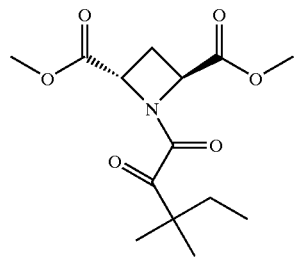

(2S,4S)-Dimethyl-1-(1,2-dioxo-3,3-dimethylpentyl)azetidine-2,4-dicarboxylate The title compound was prepared as described for Reference Example 23 except that (2S,4S)-dimethyl-1-(1,2-dioxo-2-methoxyethyl)azetidine-2,4-dicarboxylate from Reference Example 28 was used in place of (2S,4R)-dimethyl-1-(1,2-dioxo-2-methoxyethyl)azetidine-2,4-dicarboxylate. MS: 300 (M+H, 6) and 322 (M+Na, 100).

Reference Example 30

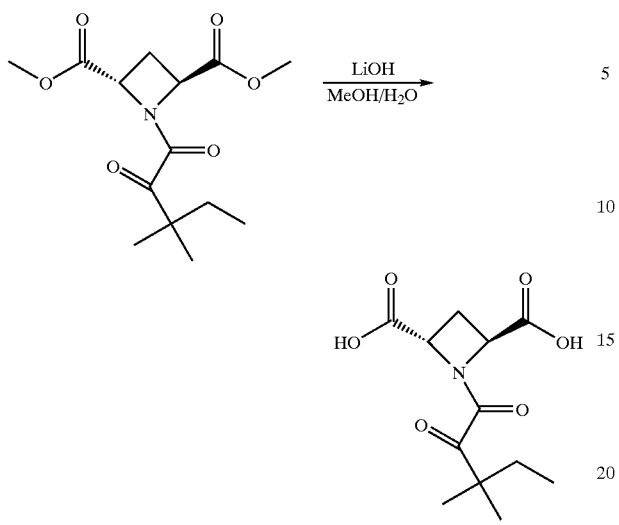

(2S,4S)-1-(1,2-dioxo-3,3-dimethylpentyl)azetidine-
2,4-dicarboxylic acid

The title compound was prepared as described for Reference Example 24 except that (2S,4S)-dimethyl-1-(1,2-dioxo-3,3-dimethylpentyl)azetidine-2,4-dicarboxylate from Reference Example 29 was used in place of (2S,4R)-dimethyl-1-(1,2-dioxo-3,3-dimethylpentyl)azetidine-2,4-dicarboxylate. MS: 270 (M−H, 100).

Compound 21

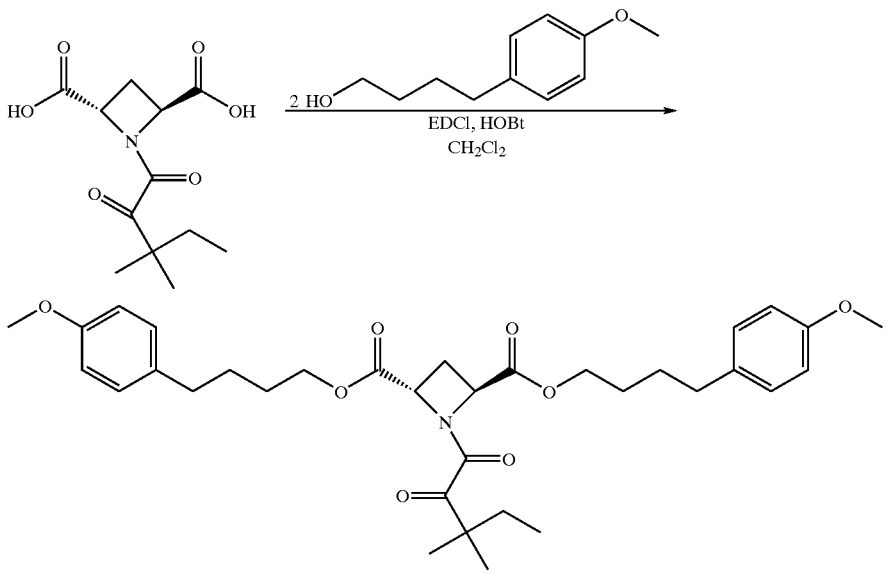

(2S,4S)-Bis-[4-(4-methoxyphenyl)-1-butyl]-1-(1,2-dioxo-3,3-dimethylpentyl)azetidine-2,4-dicarboxylate The title compound was prepared as described for Compound 16 except that (2S,4S)-1-(1,2-dioxo-3,3-dimethylpentyl)azetidine-2,4-dicarboxylate from Reference Example 30 was used in place of (2S,4R)-1-(1,2-dioxo-3,3-dimethylpentyl)azetidine-2,4-dicarboxylate (17% yield). $^1$H NMR (CDCl$_3$) δ0.79 (t, 3H, J=7.6); 1.21–1.38 (overlapped, 10H); 1.62–1.79 (overlapped, 5H); 1.82–1.93 (m, 1H); 2.42–2.64 (overlapped, 6H); 3.79 (s, 6H); 4.13–4.24 (m, 4H); 4.81 (dd, 1H, J=9.0, 6.9); 5.24 (dd, 1H, J=9.4, 6.9); 6.84 (d, 4H, J=9.4); 7.09 (d, 4H, J=10.3).

IV. Biological Assays and Activity

Examples 1 and 4 in vitro activity results are shown in Table 2. Examples 2 and 3 detail the methods used for preparation of the cell cultures used in Example 4. Example 5 in vivo activity results are shown in FIG. 1.

A. In Vitro Biological Activity

Example 1

Dorsal Root Ganalion (DRG) Culture

DRG are dissected from newborn or 1-day-old CD rats and placed into PBS on ice. After rinsing twice with sterile plating medium, DRG are transferred to empty wells of a 6-well plate coated with polyomithine/laminin (Becton Dickinson Labware) using #7 curved forceps. Three ml/well of plating medium are then added very gently, so as not to disturb the DRG. Plating medium is Leibovitz's L-15 medium (Gibco), plus 0.6% glucose, 33 mM KCl, 10% FCS, 10 mM Hepes and penicillin/streptomycin/glutamine. After overnight incubation at about 37° C. in 5% CO$_2$, this medium is replaced with 3 mL/well of assay medium [Leibovitz's L-15 medium plus 0.6% glucose, 1% FCS, 1% N-2 supplement (Gibco), 10 M ara-C, 10 mM Hepes, and penicillin/streptomycin/glutamine] containing either vehicle (DMSO, 1/200,000), positive control (2–4 ng/mL NGF) or test compound (50–250 nM). All media are prepared fresh daily. DRG are microscopically examined for neurite outgrowth on days 1–5. Under optimal conditions, vehicle treatment does not induce neurite outgrowth from DRG. An experiment is considered positive (+) if the instant compound induced neurites of ≧1 diameter of the DRG.

B. Cell Culture Assays

Example 2

Primary Rat Hippocampal Cells

Hippocampal cells are dissected from the brains of embryonic day 18 rat pups and dissociated with trypsin (1 mg/mL) and trituration. Cells are seeded at 30,000 cells/well in 96-well plates filled with 100 μL MEM and 10%FBS. At 7 days in culture, cells are fixed with 4% paraformaldehyde and immunofluorescence is performed.

Example 3

Human M17 Neuroblastoma Cells

M17 human neuroblastoma cells are cultured in 1:1 ratio of EMEM and Ham's F12 with 1×NEAA and 10% FBS. The culture media contains 1×PSN antibiotic and is exchanged every other day, and the cells are passed in log phase near confluence.

TABLE 2

In Vitro Neurotrophic Activity

| Cmpd | DRG | Rat Hippocampal Cell Response | M17 Cell Response |
| --- | --- | --- | --- |
| 1 | + | 150, 127, 115 | 140 |
| 2 | + | 108, 136 | 134 |
| 3 | NT | 119 | 110 |
| 4 | NT | NA | 107 |
| 5 | NT | NA | NA |
| 7 | NT | 123 | NT |
| 8 | NT | 182, 110, 153 | NA |
| 9 | NT | 112 | NA |
| 10 | NT | 123 | NA |
| 11 | NT | 114 | NT |
| 13 | NT | 123 | NA |
| 14 | NT | 118 | NT |
| 15 | NT | 126 | NA |
| 16 | NT | NA | 114 |
| 17 | NT | NA | 106 |
| 18 | NT | 137 | 106 |
| 19 | NT | NA | 111 |
| 20 | NT | NA | 103 |
| 21 | NT | NA | 103 |

+ = Positive results for each experiment
− = Negative results for each experiment
NA = Not active
NT = Not tested Example 4

Neurite Outgrowth Assay

Cultures are incubated with normal horse serum (1:50; Vector Labs) for about 20 min, rinsed and then incubated with primary antibody, microtubule associated-protein 2 (anti-mouse MAP-2; 1:1000; Chemicon) for about 2 h at about RT. Following primary antibody, cultures are rinsed and incubated with fluorescein anti-mouse IgG (rat absorbed; 1:50; Vector Labs) for about 1 h. After fluorescein incubation, the cultures are rinsed and read in PBS on a fluorescent plate reader (excitation: 485 nm; emission: 530 nm). A compound is regarded as active if the neurite outgrowth response is greater than the mean DMSO-treated control response on the same plate. The response to test compound is reported as percent of DMSO-treated control (absent the percentage sign). The signal-to-noise separation is consistent: the fluorescence from DMSO control wells is at least two-fold greater than blank wells.

C. In Vivo Biological Activity

Example 5

Rat Facial Nerve Compression Model

Long-Evans rats are anesthetized under ketamine (60 mg/kg)/xylazine (6 mg/kg). The facial nerve is exposed and mechanically compressed with forceps near the stylomastoid foramen unilaterally with the opposite, non-lesioned side serving as an internal control. Nerve compression causes paralysis of the whisker muscle, hence the reduced whisker movement on the lesioned side which is observed immediately after recovery from anesthesia. Rats received test compound p.o. at about 20 mg/kg twice a day for 15 days after the surgery. Control rats received vehicle only. Three to eight rats are tested in each group. Restoration of whisker movement after the treatment with compounds of the present invention is recorded at different post-operative time points daily, up to two weeks, and is shown in FIG. 1.

What is claimed is:

1. A compound of the formula:

$$A-\underset{\underset{R^1}{|}}{\square}-X\diagdown Y-Z$$

or a pharmaceutically acceptable salt thereof, wherein
  (a) $R^1$ is selected from the group consisting of
    (i) $COCOR^2$, wherein $R^2$ is $(C_1-C_6)$-straight or branched alkyl, $(C_1-C_6)$-straight or branched alkenyl, $(C_5-C_7)$-cycloalkyl, 2-thienyl, 3-thienyl, phenyl, or substituted phenyl (the substituted phenyl ring having one to three substituents independently selected from the group consisting of lower alkyl, lower alkoxy, hydroxy and halogen),
    (ii) $CONHR^3$, wherein $R^3$ is $(C_1-C_6)$-straight or branched alkyl,
    (iii) $SO_2R^4$, wherein $R^4$ is phenylalkyl or substituted phenylalkyl (the substituted phenyl ring having one to three substituents independently selected from the group consisting of lower alkyl, lower alkoxy, hydroxy and halogen), and
    (iv)

wherein the ring portion thereof is aromatic and optionally contains one or more heteroatoms selected from the group consisting of oxygen, sulfur and nitrogen;

(b) X and Y are (i) C=O and (ii) O or $NR^5$ (wherein $R^5$ is ($C_1$–$C_6$)-straight or branched alkyl), respectively, or alternatively together form a 1,5-disubstituted tetrazole ring;

(c) Z is ($C_1$–$C_5$)-straight or branched alkyl or alkenyl substituted in one or more positions with Ar, which Ar is selected from the group consisting of 2-pyridyl, 3-pyridyl, 4-pyridyl, phenyl and substituted phenyl (the substituted phenyl ring having from one to three substituents independently selected from the group consisting of lower alkyl, lower alkoxy, hydroxy and halogen), with the proviso that Z and $R^2$ cannot both be $C_1$-alkyl; and (d) A is X—Y—Z or hydrogen.

2. The compound of claim 1, wherein Z is $C_3$-straight alkyl substituted in one or more positions with 3-pyridyl.

3. The compound of claim 1, wherein $R^1$ is $COCOR^2$, $R^2$ being $C_5$-branched alkyl.

4. The compound of claim 1 having the structure

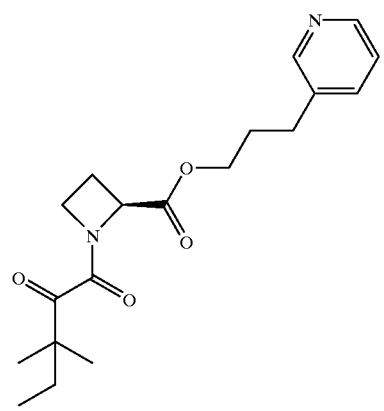

5. The compound of claim 1 having the structure

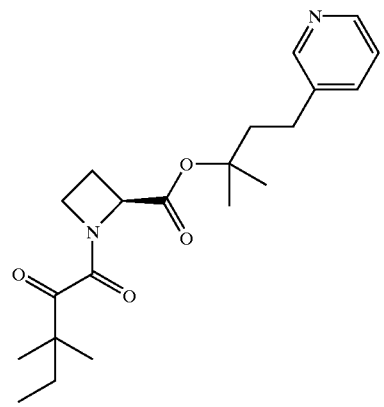

6. The compound of claim 1 having the structure

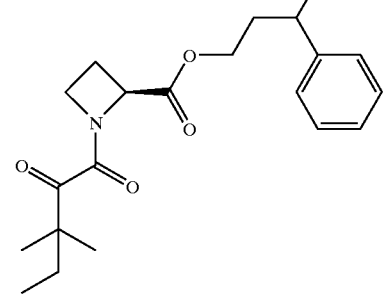

7. The compound of claim 1 having the structure

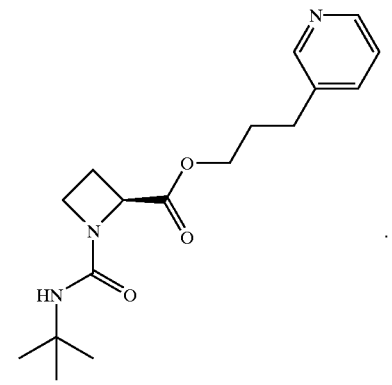

8. The compound of claim 1 having the structure

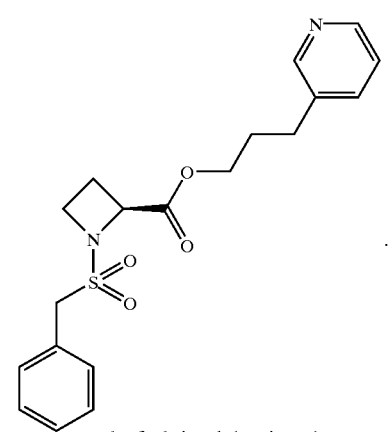

9. The compound of claim 1 having the structure

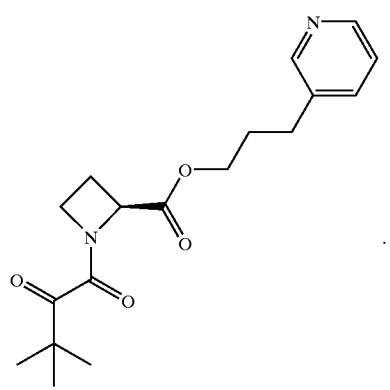

10. The compound of claim 1 having the structure

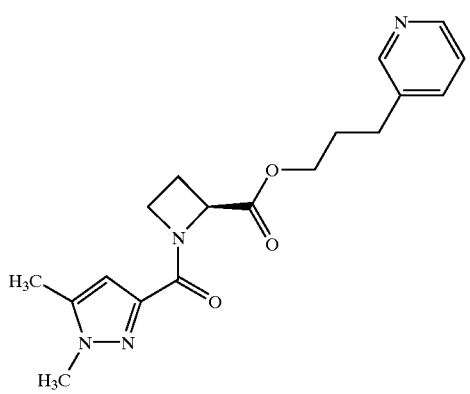

11. The compound of claim 1 having the structure

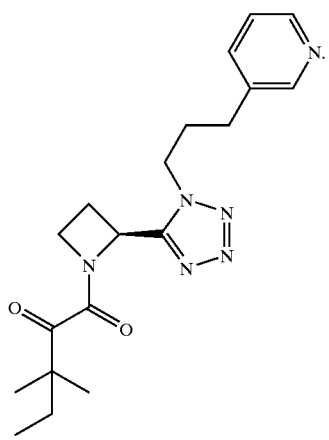

12. The compound of claim 1 having the structure

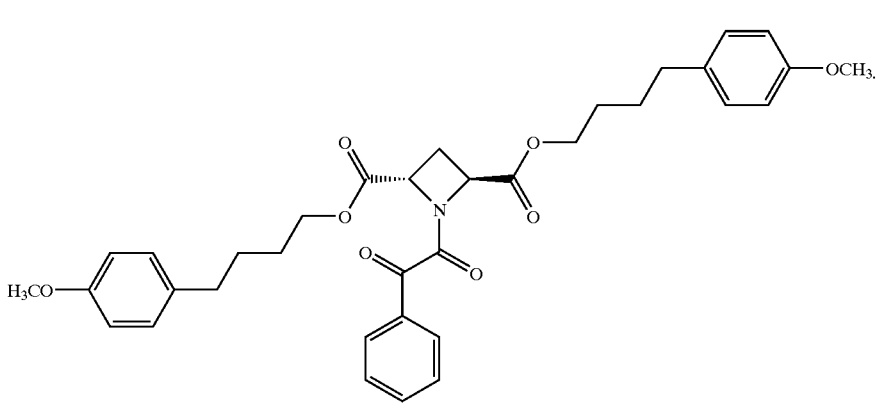

13. The compound of claim 1 having the structure

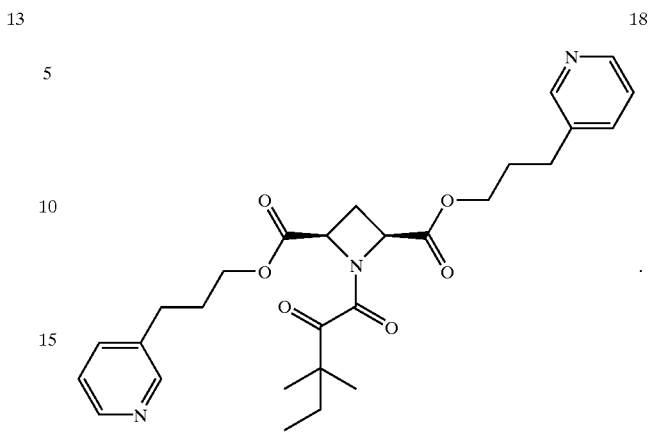

14. A method of stimulating neuronal growth comprising contacting neurons with an effective amount of the compound of claim 1.

15. A pharmaceutical composition comprising the compound of claim 1 and a pharmaceutically acceptable carrier.

16. A method of treating a subject afflicted with a disorder characterized by neuronal damage caused by disease or trauma, comprising administering to the subject a therapeutically effective amount of the pharmaceutical composition of claim 15.

17. The method of claim 16, wherein the disorder is caused by disease, and is selected from the group consisting of Parkinson's disease, Alzheimer's disease, stroke, multiple sclerosis, amyotrophic lateral sclerosis, diabetic neuropathy and Bell's palsy.

18. The method of claim 16, wherein the disorder is caused by trauma to the brain, spinal cord or peripheral nerves.

19. A method of inhibiting in a subject the onset of a disorder characterized by neuronal damage caused by disease, comprising administering to the subject a prophylactically effective amount of the pharmaceutical composition of claim 15.

20. The method of claim 19, wherein the disorder is selected from the group consisting of Parkinson's disease, Alzheimer's disease, stroke, multiple sclerosis, amyotrophic lateral sclerosis, diabetic neuropathy and Bell's palsy.

* * * * *